(12) United States Patent
Scanio et al.

(10) Patent No.: US 8,962,639 B2
(45) Date of Patent: *Feb. 24, 2015

(54) POTASSIUM CHANNEL MODULATORS

(75) Inventors: Marc J. Scanio, Lindenhurst, IL (US); William H. Bunnelle, Mundelein, IL (US); William A. Carroll, Evanston, IL (US); Sridhar Peddi, Grayslake, IL (US); Arturo Perez-Medrano, Grayslake, IL (US); Lei Shi, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 643 days.

This patent is subject to a terminal disclaimer.

(21) Appl. No.: 12/789,744

(22) Filed: May 28, 2010

(65) Prior Publication Data

US 2010/0305109 A1    Dec. 2, 2010

Related U.S. Application Data

(60) Provisional application No. 61/182,177, filed on May 29, 2009.

(51) Int. Cl.
| | | |
|---|---|---|
| C07D 239/92 | (2006.01) | |
| C07D 405/12 | (2006.01) | |
| C07D 495/04 | (2006.01) | |
| A61P 25/08 | (2006.01) | |
| A61P 25/04 | (2006.01) | |
| A61P 25/06 | (2006.01) | |
| A61P 13/06 | (2006.01) | |
| A61P 25/18 | (2006.01) | |
| A61P 25/22 | (2006.01) | |

(52) U.S. Cl.
CPC ............ *C07D 239/92* (2013.01); *C07D 405/12* (2013.01); *C07D 495/04* (2013.01)
USPC ........................................ 514/266.3; 544/287

(58) Field of Classification Search
CPC ............................ A61K 31/517; C07D 239/91
USPC ........................................ 544/287; 514/266.3
See application file for complete search history.

(56) References Cited

U.S. PATENT DOCUMENTS

| | | | |
|---|---|---|---|
| 4,252,951 A * | 2/1981 | Jackson et al. ............... 540/220 |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2005/0059823 A1 | 3/2005 | McNaughton-Smith et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| WO | WO9507271 A1 | 3/1995 |
| WO | WO9710223 A1 | 3/1997 |
| WO | WO2005099353 A2 | 10/2005 |
| WO | WO2006008754 A1 | 1/2006 |
| WO | WO2007008541 A2 | 1/2007 |

OTHER PUBLICATIONS

Vippagunta, S.R. (Adv. Drug. Delivery Rev., 2001, 48, pp. 3-26).*
Braga et al. (ChemComm, 2005, pp. 3635-3645).*
Morissette et al. (Advanced Drug Delivery Reviews, 2004, 56, pp. 275-300).*
Stella, Valentino J. (Expert Opinion of Therapeutic Patents, 2004, 14(3), pp. 277-280).*
Wolff et al. (Burger's Medicinal Chemistry, 5th Ed., 1994, vol. 1, pp. 975-977).*
Testa, Bernard (Biochemical Pharmacology, 2004, 68, pp. 2097-2106).*
Ettmayer, Peter (Medicinal Chemistry, 2004, 47(10), pp. 2394-2404).*
Klosa et al. (Journal fuer Praktische Chemie, 1966, 31(3-4), pp. 140-148).*
STN CAS search, downloaded Feb. 15, 2013, p. 1.*
Chemical Abstracts (Supplier Ambinter, Mar. 26, 2008), STN CAS search, downloaded Feb. 15, 2013, p. 1.*
Bennett G.J., et al., "A Peripheral Mononeuropathy in Rat that Produces Disorders of Pain Sensation like those Seen in Man," Pain, 1988, vol. 33 (1), pp. 87-107.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blackburn-Munro G., et al., "Retigabine: Chemical Synthesis to Clinical Application," CNS Drug Reviews, 2005, vol. 11 (1), pp. 1-20.
Blagojevic, N. et al., "Role of heavy water in Boron Neutron Capture Therapy," Topics in Dosimetry & Treatment Planning for Neutron Capture Therapy, 1994, pp. 125-134.

(Continued)

*Primary Examiner* — Susanna Moore

(57) ABSTRACT

Disclosed herein are KCNQ potassium channels modulators of formula (I)

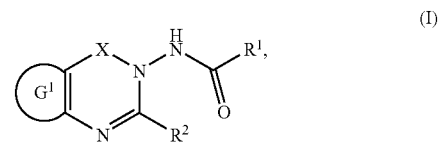

(I)

wherein ring $G^1$, X, $R^1$, and $R^2$ are as defined in the specification. Compositions comprising such compounds; and methods for treating conditions and disorders using such compounds and compositions are also described.

7 Claims, No Drawings

(56) References Cited

OTHER PUBLICATIONS

Blake, M. I. et al., "Studies With Deuterated Drugs," Journal of Pharmaceutical Sciences, 1975, vol. 64 (3), pp. 367-391.

Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

Chaplan S.R., et al., "Quantitative Assessment of Tactile Allodynia in the Rat Paw," Journal of Neuroscience Methods, 1994, vol. 53, pp. 55-63.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Czajka, D. M. et al., "Effect of Deuterium Oxide on The Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Dalby-Brown W., et al., "K(V)7 Channels: Function, Pharmacology and Channel Modulators," Current Topics in Medicinal Chemistry, 2006, vol. 6 (10), pp. 999-1023.

Database Registry Chemical Abstracts Service, Columbus, Ohio, US; 2004, XP002612331 Database accession No. 786722-52-9.

Database Registry Chemical Abstracts Service, Columbus, Ohio, US; 2008 XP002612332 Database accession No. 1005243-81-1.

Dixon W.J., "Efficient Analysis of Experimental Observations," Annual Review of Pharmacology and Toxicology, 1980, vol. 20, pp. 441-462.

Foster, A. B. et al., "Deuterium Isotope Effects in the Metabolism of Drugs and Xenobiotics: Implications for Drug Design," Advances in Drug Research, 1985, vol. 14, pp. 2-36.

Greene, T.W., et al., Protective Groups in Organic Synthesis, 3rd Edition, John Wiley and Sons, Inc., 1999, Table of Contents.

Hansen H.H., et al., "Kv7 Channels: Interaction with Dopaminergic and Serotonergic Neurotransmission in the CNS," The Journal of Physiology, 2008, vol. 586 (7), pp. 1823-1832.

Hansen H.H., et al., "The KCNQ Channel Opener Retigabine Inhibits the Activity of Mesencephalic Dopaminergic Systems of the Rat," The Journal of Pharmacology and Experimental Therapeutics, 2006, vol. 318 (3), pp. 1006-1019.

Jentsch T.J., "Neuronal KCNQ Potassium Channels: Physiology and Role in Disease," Nature Reviews Neuroscience, 2000, vol. 1 (1), pp. 21-30.

Joshi S. K., et al., "Comparison of Antinociceptive Actoins of Standard Analgesics in Attenuating Capsaicin and Nerve-Injury-Induced Mechanical Hypersensitivty," Neuroscience, 2006, vol. 143, pp. 587-596.

Kato, S. et al., "Synthesis of Deuterated Mosapride Citrate," Journal of Labelled Compounds and Radiopharmaceuticals, 1995, vol. 36 (10), pp. 927-932.

Kim S.H., et al., "An Experimental Model for Peripheral Neuropathy Produced by Segmental Spinal Nerve Ligation in the Rat," Pain, 1992, vol. 50 (3), pp. 355-363.

Kushner et al., "Pharmacological uses and perspectives of heavy water and deuterated compounds," Canadian Journal of Physiology and Pharmacology, 1999, vol. 77 (2), pp. 79-88.

Lizondo, J. et al., "Linezolid: Oxazolidinone antibacterial," Drugs of the Future, 1996, vol. 21 (11), pp. 1116-1123.

Mallesham, B. et al., "Highly Efficient Cui-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Miceli F., et al., "Molecular Pharmacology and Therapeutic Potential of Neuronal Kv7-Modulating Drugs," Current Opinion in Pharmacology, 2008, vol. 8 (1), pp. 65-74.

Munro G., et al., "Kv7 (KCNQ) Channel Modulators and Neuropathic Pain," Journal of Medicinal Chemistry, 2007, vol. 50 (11), pp. 2576-2582.

Partch, R., et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.

Poste, G. et al., "Lipid Vesicles as Carriers for Introducing Biologically Active Materials into Cells," Methods in Cell Biology, 1976, vol. 14, pp. 33-71.

Roeloffs R., et al., "In Vivo Profile of ICA-27243 [N-(6-Chloro-pyridin-3-yl)-3,4-difluoro-benzamide], a Potent and Selective KCNQ2/Q3(Kv7.2/Kv7.3) Activator in Rodent Anticonvulsant Models," The Journal of Pharmacology and Experimental Therapeutics, 2008, vol. 326 (3), pp. 818-828.

Rohde J.J., et al., "Discovery and Metabolic Stabilization of Potent and Selective 2-Amino-N-(Adamant-2-Yl) Acetamide 11beta-Hydroxysteroid Dehydrogenase Type 1 Inhibitors," Journal of Medicinal Chemistry, 2007, vol. 50 (1), pp. 149-164.

Roza C., et al., "Retigabine, the Specific KCNQ Channel Opener, Blocks Ectopic Discharges in Axotomized Sensory Fibres," Pain, 2008, vol. 138 (3), pp. 537-545.

Sotty F., et al., "Antipsychotic-Like Effect of Retigabine [N-(2-Amino-4-(Fluorobenzylamino)-Phenyl)Carbamic Acid Ester], A Kcnq Potassium Channel Opener, Via Modulation of Mesolimbic Dopaminergic Neurotransmission," The Journal of Pharmacology and Experimental Therapeutics, 2009, vol. 328 (3), pp. 951-962.

Streng T., et al., "Urodynamic Effects of the K+ Channel (KCNQ) Opener Retigabine in Freely Moving, Conscious Rats," The Journal of Urology, 2004, vol. 172 (5 pt 1), pp. 2054-2058.

Thomson, J.F., "Physiological Effects of D2O in Mammals," Annals of the New York Academy of Sciences, 1960, vol. 84, pp. 736-744.

Verma S., et al., "HIV—Associated Neuropathic Pain: Epidemiology, Pathophysiology and Management," CNS Drugs, 2005, vol. 19 (4), pp. 325-334.

Wickenden A.D., et al., "Retigabine, A Novel Anti-Convulsant, Enhances Activation of KCNQ2/Q3 Potassium Channels," Molecular Pharmacology, 2000, vol. 58 (3), pp. 591-600.

Wu, Y.J., et al., "Fluorine Substitution Can Block Cyp3a4 Metabolism-Dependent Inhibition: Identification of (S)-N-[1-(4-Fluoro-3-Morpholin-4-Ylphenyl)Ethyl]-3-(4-Fluorophenyl)Acrylamide as an Orally Bioavailable KCNQ2 Opener Devoid of Cyp3a4 Metabolism-Dependent Inhibition," The Journal of Medicinal Chemistry, 2003, vol. 46 (18), pp. 3778-3781.

Wu Y.J., et al., "(S)-N-[1-(3-Morpholin-4-Ylphenyl)Ethyl]-3-Phenylacrylamide: An Orally Bioavailable KCNQ2 Opener with Significant Activity in a Cortical Spreading Depression Model of Migraine," The Journal of Medicinal Chemistry, 2003, vol. 46 (15), pp. 3197-3200.

Model of Migraine, The Journal of Medicinal Chemistry, 2003, vol. 46 (15), pp. 3197-3200.

International Search Report and Written Opinion for PCT/2010/036596 dated Dec. 16, 2010.

* cited by examiner

POTASSIUM CHANNEL MODULATORS

This application claims priority to U.S. Patent Application Ser. No. 61/182,177, filed on May 29, 2009, and is incorporated herein by reference by its entirety.

TECHNICAL FIELD

The present invention relates to compounds that are potassium channel modulators, related pharmaceutical compositions, and methods of treating conditions and disorders using such compounds and compositions are disclosed.

BACKGROUND

Potassium channels are membrane-bound proteins responsible for regulating the flow of potassium ions through a cell membrane. The KCNQ (or $K_v7$) family is an important class of potassium channel that plays a key role in the process of neuronal excitability. There are five recognized subtypes of KCNQ channel: KCNQ1, KCNQ2, KCNQ3, KCNQ4, and KCNQ5. The KCNQ2-KCNQ5 subtypes represent the neuronal KCNQ subtypes. Miceli, *Curr. Op. Pharmacol.*, 2008, 8, 65. Functional KCNQ channels are formed by the assemblage of four individual subunits into a homotetramer or heterotetramer. The KCNQ2/3 channel is composed of a heterotetrameric assemblage of the KCNQ2 and KCNQ3 proteins.

The neuronal KCNQ channels are voltage-gated potassium channels that control cellular excitability by hyperpolarizing membrane potential, reducing action potential firing, and decreasing neurotransmitter release. Jentsch, *Nature Reviews Neurosci.*, 2000, 1, 21; Dalby-Brown, *Curr. Top. Med. Chem.*, 2006, 6, 999; Munro, *J. Med. Chem.*, 2007, 50, 2576. Neuronal KCNQ channels become activated on cellular depolarization (i.e., a change in voltage). See, Roza et al., *Pain*, 2008, 138, 537; Wickenden et al., *Mol. Pharmacol.*, 2000, 58, 591.

Activation of KCNQ channels by KCNQ openers causes an outflow of potassium ions from the cell, reducing the membrane potential (i.e., hyperpolarization), and thereby decreasing cellular excitability and action potential generation. Miceli, *Curr. Op. Pharmacol.*, 2008, 8, 65. In view of the role that KCNQ channels play in controlling cellular excitability and their distribution throughout the nervous system, KCNQ channel openers have been reported to have therapeutic utility in the treatment of a number of disorders characterized by abnormal neuronal excitability including: epilepsy, pain, migraine, anxiety, and overactive bladder. Dalby-Brown, *Curr. Top. Med. Chem.*, 2006, 6, 999; Streng, *J. Urol.*, 2004, 172, 2054. The dampening effect on neuronal excitability of KCNQ opening has also been implicated as a mechanism to inhibit the release of neurotransmitters (e.g., dopamine and serotonin) involved in schizophrenia, anxiety, and substance abuse. Hansen, *J. Physiol.* 2008, 1823.

A number of KCNQ openers, including flupirtine and retigabine, have been reported to be efficacious in treating various pain states in humans or rodents. These pain states include neuropathic pain (including diabetic polyneuropathy), inflammatory pain, persistent pain, cancer pain, and postoperative pain. Munro, *J. Med. Chem.*, 2007, 50, 2576; Dalby-Brown, *Curr. Top. Med. Chem.*, 2006, 6, 999. Thus, KCNQ openers have utility in treating a variety of painful conditions including, but not limited to, the foregoing types of pain.

The utility of KCNQ openers in the treatment of epilepsy is shown by the anticonvulsant and antiseizure activity of flupirtine, retigabine, and ICA-27243. Roeloffs, *J. Pharmacol. Exp. Ther.*, 2008, 326, 818; Miceli, *Curr. Op. Pharmacol.*, 2008, 8, 65; Blackburn-Munro, *CNS Drug Rev.*, 2005, 11, 1. Further, the utility of KCNQ openers in the treatment of migraine is indicated by the activity of KCNQ openers in an animal model of migraine. Wu, *J. Med. Chem.*, 2003, 46, 3197; Wu, *J. Med. Chem.*, 2003, 46, 3778. In addition, the utility of KCNQ openers in the treatment of HIV-associated sensory neuropathies can be found in S. Verma, L. Estanislao and D. Simpson, *CNS Drugs* 19 (2005) (4), pp. 325-334, while the utility of KCNQ openers as anxiolytics is indicated by the activity of retigabine in animal models of anxiety. Dalby-Brown, *Curr. Top. Med. Chem.*, 2006, 6, 999. Also, the utility of KCNQ openers in the treatment of schizophrenia is indicated by the ability of retigabine to inhibit the activity of dopaminergic systems (Hansen, *J. Pharmacol. Exp. Ther.*, 2006, 318, 1006; Hansen, *J. Physiol.* 2008, 1823; Sotty, *J. Pharmacol. Exp. Ther.*, 2009, 328, 951) and by retigabine's efficacy in animal models of schizophrenia. Sotty, *J. Pharmacol. Exp. Ther.*, 2009, 328, 951.

Flupirtine and retigabine both possess liabilities in terms of adverse effects including asthenia, ataxia, insomnia, headache, drowsiness, dizziness, somnolence, dry mouth, nausea, vomiting, gastric and abdominal discomfort, sedation or loss of motor coordination. Miceli, *Curr. Op. Pharmacol.*, 2008, 8, 65; Munro, *J. Med. Chem.*, 2007, 50, 2576; Blackburn-Munro, *CNS Drug Rev.*, 2005, 11, 1. These adverse effects may be related to activation of one or more KCNQ subtypes not primarily responsible for the desirable therapeutic response.

Accordingly, there is a need for KCNQ openers with efficacy in one or more of the foregoing disorders, states, or conditions, but without the side-effects of flupirtine or retigabine. KCNQ openers that selectively activate a particular subtype or subtypes can possess such efficacy with reduced side-effects.

SUMMARY OF THE INVENTION

Provided herein are compounds of formula (I)

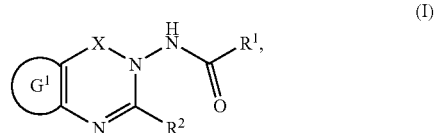

or pharmaceutically acceptable salts, solvates, prodrugs, or combinations thereof, wherein ring $G^1$ is benzo, heteroaryl, cycloalkyl, or heterocycle, each of which is independently unsubstituted or substituted with 1, 2, 3, 4, or 5 substituents as represented by T, wherein each T is independently $G^a$, alkyl, halogen, haloalkyl, oxo, —CN, —NO$_2$, —OR$^a$, —NR$^a$R$^b$, —SR$^a$, —S(O)R$^a$, —S(O)$_2$R$^a$, —C(O)R$^a$, —C(O)OR$^a$, —C(O)NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, or —(CR$^{za}$R$^{zb}$)$_m$-G$^a$;

X is C(O) or S(O)$_2$;

R$^1$ is alkyl, G$^{1a}$, or —(CR$^{1a}$R$^{1b}$)$_n$-G$^{1a}$ wherein one of CR$^{1a}$R$^{1b}$ groups can optionally be replaced by O, N(H), N(alkyl), S, S(O), or S(O)$_2$;

R$^2$ is hydrogen, alkyl, haloalkyl, —OR$^{2c}$, —SR$^{2c}$, —S(O)R$^{2c}$, —S(O)$_2$R$^{2c}$, —N(R$^{2d}$)(R$^{2e}$), G$^{2a}$, —(CR$^{za}$R$^{zb}$)$_p$-G$^{2a}$, —(CR$^{2a}$R$^{2b}$)$_p$—OR$^{2c}$, —(CR$^{2a}$R$^{2b}$)$_p$—SR$^{2c}$, —(CR$^{2a}$R$^{2b}$)$_p$—S(O)R$^{2c}$, or —(CR$^{2a}$R$^{2b}$)$_p$—S(O)$_2$R$^{2c}$;

R$^{2c}$, at each occurrence, is independently hydrogen, alkyl, haloalkyl, G$^{2a}$, or —(CR$^{2a}$R$^{2b}$)$_p$-G$^{2a}$;

R$^{2d}$ and R$^{2e}$, are each independently hydrogen, alkyl, haloalkyl, -alkylenyl-alkoxy, -alkylenyl-haloalkoxy, or -alkylenyl-CN;

G$^{1a}$ and G$^{2a}$, at each occurrence, are each independently aryl, heteroaryl, heterocycle, monocyclic cycloalkyl, or polycyclic cycloalkyl; each of which is independently unsubstituted or substituted with 1, 2, 3, or 4 substituents independently selected from the group consisting of G$^a$, alkyl, halogen, haloalkyl, oxo, —CN, —NO$_2$, —OR$^a$, —NR$^a$R$^b$, —SR$^a$, —S(O)R$^a$, —S(O)$_2$R$^a$, —C(O)R$^a$, —C(O)OR$^a$, —C(O)NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$, —(CR$^{za}$R$^{zb}$)$_m$—SR$^a$, —(CR$^{za}$R$^{zb}$)$_m$—S(O)$_2$R$^a$, —(CR$^{za}$R$^{zb}$)$_m$—C(O)R$^a$, and —(CR$^{za}$R$^{zb}$)$_m$—C(O)NR$^a$R$^b$;

G$^a$, at each occurrence, is independently aryl or C$_3$-C$_6$ cycloalkyl; each of which is independently unsubstituted or substituted with 1, 2, or 3 substituents selected from the group consisting of alkyl, halogen, haloalkyl, oxo, —CN, —NO$_2$, —OR$^a$, —NR$^a$R$^b$, —SR$^a$, —S(O)R$^a$, —S(O)$_2$R$^a$, —C(O)R$^a$, —C(O)OR$^a$, —C(O)NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$ (CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—C(O)R$^a$, —(CR$^{za}$R$^{zb}$)$_m$—C(O)OR$^a$, and —(CR$^{za}$R$^{zb}$)$_m$—C(O)NR$^a$R$^b$;

R$^a$ and R$^b$, at each occurrence, are each independently hydrogen, alkyl, or haloalkyl;

R$^{1a}$ and R$^{1b}$, at each occurrence, are each independently hydrogen, alkyl, halogen, or haloalkyl; wherein R$^{1a}$ and R$^{1b}$, together with the carbon atom(s) to which they are attached, optionally form a 3-, 4-, 5-, or 6-membered monocyclic cycloalkyl when R$^{1a}$ and R$^{1b}$ are independently alkyl or haloalkyl;

R$^{za}$, R$^{zb}$, R$^{2a}$, and R$^{2b}$, at each occurrence, are each independently hydrogen, alkyl, halogen, or haloalkyl; and m, n, and p, at each occurrence, are each independently 1, 2, 3, or 4;

with the proviso that when
R$^1$ is alkyl, G$^{1a}$, or —(CR$^{1a}$R$^{1b}$)$_n$-G$^{1a}$; wherein G$^{1a}$ is other than polycyclic cycloalkyl, then
R$^2$ is —OR$^{2c}$, —SR$^{2c}$, —S(O)R$^{2c}$, —S(O)$_2$R$^{2c}$, G$^{2a}$, —(CR$^{2a}$R$^{2b}$)$_p$-G$^{2a}$, —(CR$^{2a}$R$^{2b}$)$_p$—OR$^{2c}$, —(CR$^{2a}$R$^{2b}$)$_p$—SR$^{2c}$, —(CR$^{2a}$R$^{2b}$)$_p$—S(O)R$^{2c}$, or —(CR$^{2a}$R$^{2b}$)$_p$—S(O)$_2$R$^{2c}$, wherein R$^{2c}$, at each occurrence, is independently G$^{2a}$ or —(CR$^{2a}$R$^{2b}$)$_p$-G$^{2a}$; and
G$^{2a}$ is polycyclic cycloalkyl;
and with the further proviso that when
R$^2$ is hydrogen, alkyl, haloalkyl, —OR$^{2c}$, —SR$^{2c}$, —S(O)R$^{2c}$, —S(O)$_2$R$^{2c}$, —N(R$^{2d}$)(R$^{2e}$), G$^{2a}$, —(CR$^{2a}$R$^{2b}$)$_p$-G$^{2a}$, —(CR$^{2a}$R$^{2b}$)$_p$—OR$^{2c}$, —(CR$^{2a}$R$^{2b}$)$_p$—SR$^{2c}$, —(CR$^{2a}$R$^{2b}$)$_p$—S(O)R$^{2c}$, or —(CR$^{2a}$R$^{2b}$)$_p$—S(O)$_2$R$^{2c}$; wherein R$^{ea}$, at each occurrence, is independently hydrogen, alkyl, haloalkyl, G$^{2a}$, or —(CR$^{2a}$R$^{2b}$)$_p$-G$^{2a}$; and
G$^{2a}$ is other than polycyclic cycloalkyl,
then R$^1$ is G$^{1a}$ or —(CR$^{1a}$R$^{1b}$)$_n$-G$^{1a}$; wherein G$^{1a}$ is polycyclic cycloalkyl.

Compounds described herein or pharmaceutically acceptable salts or solvates thereof are KCNQ channel modulators and are thus useful in the treatment of diseases, disorders, or conditions of a subject through the modulation of KCNQ channels.

Another aspect is related to pharmaceutical compositions comprising therapeutically effective amounts of one or more compound(s) described herein or pharmaceutically acceptable salts or solvates thereof, in combination with one or more pharmaceutically acceptable carrier(s). Such compositions can be administered in accordance with a method of the invention, typically as part of a therapeutic regimen for treatment or prevention of conditions and disorders related to the modulation of KCNQ channels. More particularly, the methods are useful for treating disorders or conditions related to pain such as neuropathic pain (including diabetic polyneuropathy, HIV-associated sensory neuropathies), nociceptive pain, post-operative pain, persistent pain, osteoarthritic pain, cancer pain, inflammatory pain, migraine, and postoperative pain, as well as epilepsy, overactive bladder, schizophrenia, anxiety, and substance abuse.

Further provided herein are the use of the present compounds or pharmaceutically acceptable salts or solvates thereof, in the manufacture of a medicament for the treatment of the disease conditions described above, alone or in combination with one or more pharmaceutically acceptable carrier(s), particularly for the treatment or alleviation of disorders or conditions related to pain such as neuropathic pain (including diabetic polyneuropathy, HIV-associated sensory neuropathies), nociceptive pain, post-operative pain, persistent pain, osteoarthritic pain, cancer pain, inflammatory pain, postoperative pain, and migraine, epilepsy, overactive bladder, schizophrenia, anxiety, and substance abuse.

The compounds or salts or solvates thereof, compositions comprising the compounds or pharmaceutically acceptable salts or solvates thereof, and methods for treating or preventing conditions and disorders by administering the compounds or salts or solvates thereof, or by administering the compositions thereof are further described herein.

These and other objectives of the invention are described in the following paragraphs. These objectives should not be deemed to narrow the scope of the invention.

DETAILED DESCRIPTION OF THE INVENTION

Provided are compounds of formula (I)

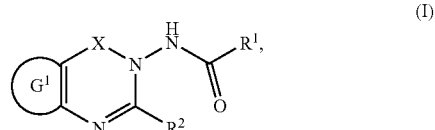

(I)

wherein G$^1$, R$^1$, R$^2$, and X are as defined above in the Summary and below in the Detailed Description. Compositions comprising such compounds and methods for treating conditions and disorders using such compounds and compositions are also disclosed.

In various embodiments, there can be variables that occur more than one time in any substituent or in the compound or any other formulae herein. Definition of a variable on each occurrence is independent of its definition at another occurrence. Further, combinations of variables or substituents are permissible only if such combinations result in stable compounds. Stable compounds are compounds that can be isolated from a reaction mixture.

a. Definitions

It is noted that, as used in this specification and the intended claims, the singular form "a," "an," and "the" includes plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a saturated, straight or branched hydrocarbon chain containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a saturated, straight or branched hydrocarbon chain of from 1 to 10 carbon atoms. Representative examples of alkylene include, but are not limited to, —CH$_2$—, —CH(CH$_3$)—, —CH(C$_2$H$_5$)—, —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl (including 1,2,3,4-tetrahydronaphthalen-1-yl). The phenyl and the bicyclic aryls are attached to the parent molecular moiety through any carbon atom contained within the phenyl or the bicyclic aryls respectively.

The term "cycloalkenyl" as used herein, means a monocyclic hydrocarbon ring system containing three-, four-, five-, six-, seven-, or eight carbon atoms and zero heteroatoms in the ring. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. The cycloalkenyl groups are appended to the parent molecular moiety through any substitutable carbon atom within the groups.

The term "cycloalkyl" as used herein, means a monocyclic, or a bicyclic cycloalkyl, or a spirocyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl ring. An example of a spirocyclic cycloalkyl is spiro[2.5]octane. The monocyclic, bicyclic, and spirocyclic cycloalkyl groups are appended to the parent molecular moiety through any substitutable carbon atom of the groups.

The term "polycyclic cycloalkyl" as used herein, means a monocyclic cycloalkyl or a bicyclic cycloalkyl as defined herein, wherein one or two pairs of non-adjacent carbon atoms within the monocyclic and bicyclic cycloalkyl ring system are linked by one or two alkylene bridge(s) of 1, 2, 3, or 4 carbon atoms respectively. The polycyclic cycloalkyls described herein can optionally contain 1 or 2 double bonds. One or two carbon atoms of the alkylene bridge(s) and/or one or two ring carbon atom(s) of the polycyclic cycloalkyl is optionally replaced by heteroatom(s) selected from O, N or S, wherein the nitrogen and sulfur atoms are optionally oxidized, and the nitrogen atom(s) are optionally quarternized. Non-limiting examples of the polycyclic cycloalkyls include, tricyclo[3.2.1.0$^{2,4}$]oct-3-yl, hexahydro-2,5-methano-3a(1H)-pentalene (noradamantane or octahydro-2,5-methanopentalene), bicyclo[2.2.1]heptane, bicyclo[2.2.1]heptene, bicyclo[2.2.2]octane, bicyclo[3.3.1]nonane, bicyclo[3.2.1]octane, adamantane (tricyclo[3.3.1.1$^{3,7}$]decane), oxadamantane (oxatricyclo[3.3.1.1$^{3,7}$]decane), azaadamantane, and azabicyclo[2.2.1]heptane.

The term "halo" or "halogen" as used herein, means —Cl, —Br, —I or —F.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "haloalkoxy" as used herein, means an alkoxy group as defined herein, in which one, two, three, four, five, six, or seven hydrogen atoms are replaced by halogen. Non-limiting examples of haloalkoxy include trifluoromethoxy, 2,2,2-trifluoroethoxy, and 2-fluoroethoxy.

The term "heteroaryl" as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, 5,6-dihydro-4H-cyclopenta[b]thiophene, 4,5,6,7-tetrahydrobenzo[b]thiophene, 5,6,7,8-tetrahydro-4H-cyclohepta[b]thiophene, chromenyl, cinnolinyl, furopyridine, indolyl, indazolyl, isoindolyl, isoquinolinyl, naphthyridinyl, oxazolopyridine, quinolinyl, quinazolinyl, quinoxalinyl, and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings can optionally be oxidized and the nitrogen atoms can optionally be quaternized, and are contemplated within the scope of the invention.

The term "heterocycle" or "heterocyclic" as used herein, means a monocyclic, bicyclic, or a spirocyclic ring system containing at least one heteroatom. The monocyclic heterocycle is a 3-, 4- 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Representative examples of monocyclic heterocycles include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxol-4-yl, 1,3-benzodithiolyl, 2,3-dihydro-1,4-benzodioxinyl, 2,3-dihydrobenzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro[3,4]octane. The heterocycle groups are connected to the parent molecular moiety through any substitutable carbon atom or any substitutable nitrogen atom contained within the group. The nitrogen and sulfur heteroatoms in the heterocycle rings can optionally be oxidized (e.g. 1,1-dioxidothiomorpholinyl (thiomorpholine sulfone)) and the nitrogen atoms can optionally be quaternized.

In some instances, the number of carbon atoms in a substituent (e.g., alkyl, alkenyl, alkynyl, alkoxy, haloalkoxy, or cycloalkyl) is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms. Illustrating further, $C_3$-$C_6$ cycloalkyl means a monocyclic cycloalkyl as defined herein above containing from 3 to 6 carbon ring atoms.

If a substituent is described as being optionally substituted with up to a particular number of non-hydrogen radicals, that substituent can be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 5 non-hydrogen radicals, then any heteroaryl with less than 5 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical.

The term "heteroatom" means N, O, or S.

The term "oxo" means =O.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "modulate" refers to the ability of a compound to increase or decrease the function, or activity, of KCNQ channels. "Modulation", as used herein in its various forms, is intended to encompass antagonism, agonism, partial antagonism and/or partial agonism of the activity associated with KCNQ channels. KCNQ channels activators are compounds that, e.g., bind to, stimulate, increase, open, activate, or facilitate KCNQ channels such as, but not limited to, KCNQ2 and/or KCNQ3 potassium channels. Activation of KCNQ channels encompasses either or both of: (1) increasing current through a KCNQ channel; or (2) shifting the half-activation potential of KCNQ channels to lower voltages (i.e. a hyperpolarizing shift of the V1/2 for activation).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. Compounds

KCNQ channel modulators have formula (I) as described above.

Particular values of variable groups in compounds of formula (I) are as follows. Such values can be used where appropriate with any of the other values, definitions, claims or embodiments defined hereinbefore or hereinafter.

In compounds of formula (I), ring $G^1$ has values as disclosed in the Summary.

In certain embodiments, ring $G^1$ is optionally substituted benzo, thus, included herein are compounds of formula (I-a)

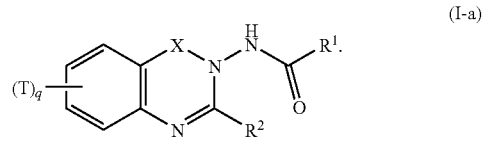

(I-a)

In certain embodiments, ring $G^1$ is optionally substituted heteroaryl. Examples of such heteroaryl include, but are not limited to, 5,6-dihydro-4H-cyclopenta[b]thiophene, 4,5,6,7-tetrahydrobenzo[b]thiophene, 5,6,7,8-tetrahydro-4H-cyclohepta[b]thiophene, thiophene,1 and pyrazol, each of which is optionally substituted as described in the Summary and embodiments herein. Examples of compounds of formula (I) containing such rings include but are not limited to those represented by formula (I-b), (I-c), (I-d), and (I-e):

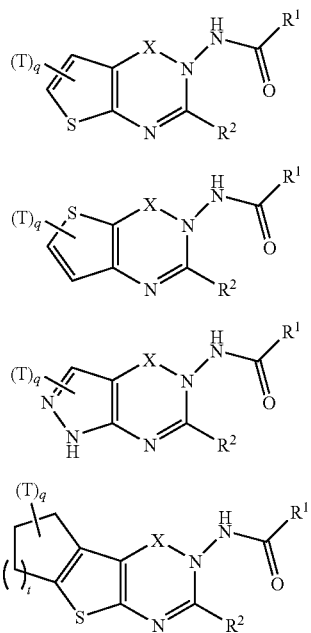

In compounds of formula (I-a)-(I-e), q is 0, 1, 2, 3, or 4, t is 1, 2, or 3, and T, X, $R^1$, and $R^2$ are as described in the Summary and in the embodiments herein.

T, when present, is attached to any substitutable carbon or nitrogen atom of the ring $G^1$ and has values as described in the Summary.

For example, certain compounds of formula (I), (I-a)-(I-e) include those wherein T is absent.

Yet certain compounds of formula (I), (I-a)-(I-e) include those wherein T, at each occurrence, is independently halogen (e.g. Cl, Br, F), alkyl (e.g. $C_1$-$C_6$ alkyl such as, but not limited to, ethyl, methyl), $G^a$ (e.g. optionally substituted aryl such as, but not limited to, optionally substituted phenyl), or haloalkyl (including but not limited thereto, trifluoromethyl).

In conjunction with any above or below embodiments, T, if present, is —F.

In conjunction with any above or below embodiments, X is as described in the Summary and herein below. For example, in certain embodiments, compounds of formula (I), (I-a)-(I-e) include those wherein X is C(O). In other embodiments, X is $S(O)_2$.

$R^1$ and $R^2$ for compounds of formula (I), (I-a)-(I-e) have values as described in the Summary.

Certain embodiments are directed to a group of compounds of formula (I), (I-a)-(I-e) wherein $R^2$ is $G^{1a}$ and $G^{2a}$ is optionally substituted polycyclic cycloalkyl. In conjunction with any above or below embodiments, a non limiting example of said optionally substituted polycyclic cycloalkyl includes, but is not limited to, optionally substituted hexahydro-2,5-methano-3a(1H)-pentalene.

Certain embodiments are directed to a group of compounds of formula (I), (I-a)-(I-e) wherein $R^2$ is (a). hydrogen,
(b). alkyl (e.g. $C_1$-$C_6$ alkyl such as, but not limited to, methyl, ethyl, isopropyl),
(c). —$SR^{2c}$ wherein $R^{2c}$ is alkyl;
(d). $G^{2a}$ wherein $G^{2a}$ is other than polycyclic cycloalkyl;
(e). —$OR^{2c}$ wherein $R^{2c}$ is as described in the Summary;
(f) —$(CR^{2a}R^{2b})_p$—$OR^{2c}$ wherein $R^{2a}$, $R^{2b}$, p, and $R^{2c}$ are as described in the Summary;

(g). —$N(R^{2d})(R^{2e})$ wherein $R^{2d}$ and $R^{2e}$ are as described in the Summary; or
(h) haloalkyl.

In the compounds wherein $R^2$ is —$OR^{2c}$ or —$(CR^{2a}R^{2b})_p$—$OR^{2c}$, examples of $R^{2c}$ included, but not limited to, hydrogen or —$(CR^{2a}R^{2b})_p$-$G^{2a}$ wherein $R^{2a}$, $R^{2b}$, and p are as described in the Summary, and $G^{2a}$ is other than polycyclic cycloalkyl. For example, $G^{2a}$ in the aforementioned embodiments is aryl, heteroaryl, heterocycle, or monocyclic cycloalkyl, each of which is optionally substituted. For example, $G^{2a}$ is optionally substituted aryl (such as, but not limited to, optionally substituted phenyl) or optionally substituted monocyclic cycloalkyl (for example but not limited thereto, optionally substituted $C_3$-$C_6$ cycloalkyl such as, but not limited to, cyclopropyl).

In certain embodiments, $R^2$ is
(a). hydrogen,
(b). alkyl (e.g. $C_1$-$C_6$ alkyl such as, but not limited to, methyl, ethyl, isopropyl),
(c). —$SR^{2c}$ wherein $R^{2c}$ is $C_1$-$C_6$ alkyl;
(d). $G^{2a}$ (e.g. optionally substituted aryl such as but not limited to, optionally substituted phenyl, or optionally substituted monocyclic cycloalkyl such as but not limited thereto, optionally substituted $C_3$-$C_6$ cycloalkyl); $G^{2a}$, for example is optionally substituted phenyl, other examples of $G^{2a}$ is optionally substituted $C_3$-$C_6$ cycloalkyl such as, but not limited to, optionally substituted cyclopropyl;
(e). —$OR^{2c}$ wherein $R^{2c}$ is hydrogen,
(f). —$(CR^{2a}R^{2b})_p$—$OR^{2c}$ (e.g. —$(CR^{2a}R^{2b})_p$—OH or —$(CR^{2a}R^{2b})_p$—O—$(CR^{2a}R^{2b})_p$-$G^{2a}$ wherein $G^{2a}$ is optionally substituted aryl such as but not limited to, optionally substituted phenyl);
(g). —$N(R^{2d})(R^{2e})$ wherein $R^{2d}$ and $R^{2e}$ are each independently hydrogen or $C_1$-$C_6$ alkyl such as but not limited to, methyl, ethyl, or isopropyl; or
(h). haloalkyl such as $C_1$-$C_6$ halolakyl (e.g. trifluoromethyl, 2,2,2-trifluoroethyl).

In certain embodiments, $R^2$ is hydrogen or alkyl (e.g $C_1$-$C_6$ alkyl such as, but not limited to, methyl, ethyl, isopropyl).

In certain embodiments, $R^2$ is alkyl (e.g $C_1$-$C_6$ alkyl such as, but not limited to, methyl, ethyl, isopropyl).

Certain embodiments are directed to a group of compounds of formula (I), (I-a)-(I-e) wherein $R^1$ is $G^{1a}$ or —$(CR^{1a}R^{1b})_n$-$G^{1a}$; and $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and in embodiments described herein below.

Still other embodiments are directed to a group of compounds of formula (I), (I-a)-(I-e) wherein $R^1$ is $G^{1a}$ wherein $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and in embodiments described herein below.

Still other embodiments are directed to a group of compounds of formula (I), (I-a)-(I-e) wherein $R^1$ is —$(CR^{1a}R^{1b})_n$-$G^{1a}$ wherein $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and in embodiments described herein below.

Yet other embodiments are directed to a group of compounds of formula (I), (I-a)-(I-e) wherein $R^1$ is alkyl (e.g. $C_1$-$C_6$ alkyl such as, but not limited to, methyl) or —$(CR^{1a}R^{1b})_n$-$G^{1a}$, and $G^{1a}$ is other than polycyclic cycloalkyl that is optionally substituted. For example, $G^{1a}$ is optionally substituted aryl or optionally substituted $C_3$-$C_6$ cycloalkyl (e.g. optionally substituted cyclopentyl).

In conjunction with any above or below embodiments, non limiting examples of said optionally substituted polycyclic cycloalkyl of $G^{1a}$ include, but are not limited to, optionally substituted hexahydro-2,5-methano-3a(1H)-pentalene, optionally substituted adamantane, unsubstituted bicyclo[2.2.1]heptane, unsubstituted bicyclo[2.2.1]heptene, optionally substituted oxatricyclo[3.3.1.1$^{3,7}$]decane, unsubstituted bicyclo[3.2.1]octane, bicyclo[3.3.1]nonane unsubstituted or substituted with one oxo group, and unsubstituted tricyclo [3.2.1.0$^{2,4}$]octane.

In conjunction with any above or below embodiments, examples of said optionally substituted polycyclic cycloalkyl of $G^{1a}$ is unsubstituted bicyclo[2.2.1]heptane, unsubstituted adamantane, or adamantane substituted with a halogen group.

n, p, $R^{1a}$, $R^{1b}$, $R^{2a}$, $R^{2b}$, and the optional substituents of $G^{1a}$ and $G^{1a}$ are as described in the Summary and herein. In conjunction with any above or below embodiments, n, for example, is 1 or 2. In certain embodiments, n is 1. In conjunction with any above or below embodiments, $R^{1a}$, $R^{1b}$, $R^{2a}$, $R^{2b}$ are each for example, independently hydrogen or $C_1$-$C_6$ alkyl, for example, hydrogen. In conjunction with any above or below embodiments, examples of the optional substituents of $G^{1a}$ and $G^{1a}$ include, but are not limited to, halogens.

It is appreciated that compounds of formula (I), (I-a)-(I-e) with combinations of the above embodiments, including particular, more particular and preferred embodiments are contemplated.

Accordingly, one aspect relates to a group of compounds of formula (I), (I-a)-(I-e) wherein X is C(O), $R^2$ is $G^{1a}$, and $G^{2a}$ is optionally substituted polycyclic cycloalkyl.

Still another aspect relates to a group of compounds of formula (I), (I-a)-(I-e) wherein X is S(O)$_2$, $R^2$ is $G^{1a}$, and $G^{2a}$ is optionally substituted polycyclic cycloalkyl.

Within each group of compounds of formula (I), (I-a)-(I-e) as described in the preceding paragraphs, $R^1$, and the optional substituents of $G^{2a}$ are as described generally in the Summary and in embodiments described above and herein. In certain embodiments, $G^{2a}$ is unsubstituted.

Thus, of each group of compounds of formula (I), (I-a)-(I-e) as described in the preceding paragraphs, examples of a subgroup include those wherein $R^1$ is $G^{1a}$ or —(CR$^{1a}$R$^{1b}$)$_n$-$G^{1a}$; and $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Examples of another subgroup include those wherein $R^1$ is $G^{1a}$, and $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Examples of yet another subgroup include those wherein $R^1$ is —(CR$^{1a}$R$^{1b}$)$_n$-$G^{1a}$, and $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Examples of another subgroup of compounds of formula (I), (I-a)-(I-e) include those wherein $R^1$ is alkyl (e.g. $C_1$-$C_6$ alkyl such as, but not limited to, methyl) or —(CR$^{1a}$R$^{1b}$)$_n$-$G^{1a}$, and $G^{1a}$ is aryl, heteroaryl, heterocycle, or monocyclic cycloalkyl, each of which is optionally substituted. For example, $G^{1a}$ is optionally substituted aryl (e.g. optionally substituted phenyl) or optionally substituted $C_3$-$C_6$ cycloalkyl (e.g. cyclopentyl). In certain embodiments, $G^{1a}$ is optionally substituted aryl (e.g. optionally substituted phenyl). In other embodiments, $G^{1a}$ is optionally substituted $C_3$-$C_6$ cycloalkyl (e.g. cyclopentyl).

Another aspect relates to a group of compounds of formula (I), (I-a)-(I-e) wherein X is C(O); $R^1$ is $G^{1a}$ or —(CR$^{1a}$R$^{1b}$)$_n$-$G^{1a}$; and $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Another aspect relates to a group of compounds of formula (I), (I-a)-(I-e) wherein X is C(O), $R^1$ is $G^{1a}$ wherein $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Yet another aspect relates to a group of compounds of formula (I), (I-a)-(I-e) wherein X is C(O), $R^1$ is —(CR$^{1a}$R$^{1b}$)$_n$-$G^{1a}$ wherein $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Another aspect relates to a group of compounds of formula (I), (I-a)-(I-e) wherein X is S(O)$_2$; $R^1$ is $G^{1a}$ or —(CR$^{1a}$R$^{1b}$)$_n$-$G^{1a}$; and $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Another aspect relates to a group of compounds of formula (I), (I-a)-(I-e) wherein X is S(O)$_2$; $R^1$ is $G^{1a}$ wherein $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Yet another aspect relates to a group of compounds of formula (I), (I-a)-(I-e) wherein X is S(O)$_2$; $R^1$ is —(CR$^{1a}$R$^{1b}$)$_n$-$G^{1a}$ wherein $G^{1a}$ is optionally substituted polycyclic cycloalkyl. In certain embodiments, $G^{1a}$ is unsubstituted polycyclic cycloalkyl. In certain embodiments, $G^{1a}$ is polycyclic cycloalkyl substituted as described in the Summary and embodiments herein above.

Within each group of compounds of formula (I), (I-a)-(I-e) as described in the preceding six paragraphs, $R^2$, $R^{1a}$, $R^{1b}$, n, and the optional substituents of $G^{1a}$ are as described generally in the Summary and in embodiments described above and herein.

Thus, of each group of compounds of formula (I), (I-a)-(I-e) as described in the preceding six paragraphs, examples of a subgroup include those wherein $R^2$ is (a). hydrogen, (b). alkyl (e.g. $C_1$-$C_6$ alkyl such as, but not limited to, methyl, ethyl, isopropyl), (c). —SR$^{2c}$ wherein R$^{2c}$ is alkyl;

(d). $G^{2a}$ wherein $G^{2a}$ is other than polycyclic cycloalkyl;

(e). —OR$^{2c}$ wherein R$^{2c}$ is as described in the Summary;

(f) —(CR$^{2a}$R$^{2b}$)$_p$—OR$^{2c}$ wherein R$^{2a}$, R$^{2b}$, p, and R$^{2c}$ are as described in the Summary;

(g). —N(R$^{2d}$)(R$^{2e}$) wherein R$^{2d}$ and R$^{2e}$ are as described in the Summary; or (h) haloalkyl.

In the compounds wherein R$^2$ is —OR$^{2c}$ or —(CR$^{2a}$R$^{2b}$)$_p$—OR$^{2c}$, examples of R$^{2c}$ include, but not limited to, hydrogen —(CR$^{2a}$R$^{2b}$)$_p$-G$^{2a}$ wherein R$^{2a}$, R$^{2b}$, and p are as described in the Summary, and G$^{2a}$ is other than polycyclic cycloalkyl. For example, G$^{2a}$ in the aforementioned embodiments is aryl, heteroaryl, heterocycle, or monocyclic cycloalkyl, each of which is optionally substituted. For example, G$^{2a}$ is optionally substituted aryl (such as, but not limited to, optionally substituted phenyl) or optionally substituted monocyclic cycloalkyl (for example but not limited thereto, optionally substituted C$_3$-C$_6$ cycloalkyl such as, but not limited to, cyclopropyl).

Examples of another subgroup include those wherein R$^2$ is
(a). hydrogen,
(b). alkyl (e.g. C$_1$-C$_6$ alkyl such as, but not limited to, methyl, ethyl, isopropyl),
(c). —SR$^{2c}$ wherein R$^{2c}$ is C$_1$-C$_6$ alkyl;
(d). G$^{2a}$ (e.g. optionally substituted aryl such as but not limited to, optionally substituted phenyl, or optionally substituted monocyclic cycloalkyl such as but not limited thereto, optionally substituted C$_3$-C$_6$ cycloalkyl); in certain embodiments, G$^{2a}$ is optionally substituted phenyl; yet in other embodiments, G$^{2a}$ is optionally substituted C$_3$-C$_6$ cycloalkyl (e.g. optionally substituted cyclopropyl);
(e). —OR$^{2c}$ wherein R$^{2c}$ is hydrogen,
(f). —(CR$^{2a}$R$^{2b}$)$_p$—OR$^{2c}$ (e.g. —(CR$^{2a}$R$^{2b}$)$_p$—OH or —(CR$^{2a}$R$^{2b}$)$_p$—O—(CR$^{2a}$R$^{2b}$)$_p$-G$^{2a}$ wherein G$^{2a}$ is optionally substituted aryl such as but not limited to, optionally substituted phenyl);
(g). —N(R$^{2d}$)(R$^{2e}$) wherein R$^{2d}$ and R$^{2e}$ are each independently hydrogen or C$_1$-C$_6$ alkyl such as but not limited to, methyl, ethyl, or isopropyl; or
(h). haloalkyl such as C$_1$-C$_6$ halolakyl (e.g. trifluoromethyl, 2,2,2-trifluoroethyl).

Examples of yet another subgroup include those wherein R$^2$ is hydrogen or alkyl (e.g C$_1$-C$_6$ alkyl such as, but not limited to, methyl, ethyl, isopropyl).

Examples of yet another subgroup include those wherein R$^2$ is alkyl (e.g C$_1$-C$_6$ alkyl such as, but not limited to, methyl, ethyl, isopropyl).

Within each group and subgroup of compounds of formula (I), (I-a)-(I-e) as described herein above, n, p, R$^{1a}$, R$^{1b}$, R$^{2a}$, R$^{2b}$, and the optional substituents of G$^{1a}$ and G$^{2a}$ have values as described generally in the Summary and specifically in embodiments herein above.

Contemplated herein are, for example, compounds of formula (I), (I-a)-(I-e) wherein
R$^1$ is —(CR$^{1a}$R$^{1b}$)$_n$-G$^{1a}$;
R$^{1a}$ and R$^{1b}$ are hydrogen,
n is 1,
G$^{1a}$ is optionally substituted polycyclic cycloalkyl (e.g. unsubstituted bicyclo[2.2.1]heptane, unsubstituted adamantane, or adamantane substituted with one halogen group),
R$^2$ is alkyl;
X is C(O),
q is 0 or 1; and
T is —F.

Exemplary compounds contemplated include, but are not limited to:
2-(2-adamantyl)-N-(2-isopropyl-4-oxoquinazolin-3(4H)-yl)acetamide;
2-(4-chlorophenyl)-N-(2-hexahydro-2,5-methanopentalen-3a(1H)-yl-4-oxoquinazolin-3(4H)-yl)acetamide;
3-cyclopentyl-N-(2-hexahydro-2,5-methanopentalen-3a(1H)-yl-4-oxoquinazolin-3(4H)-yl)propanamide;
N-(2-hexahydro-2,5-methanopentalen-3a(1H)-yl-4-oxoquinazolin-3(4H)-yl)acetamide;
2-(1-adamantyl)-N-(2-isopropyl-4-oxoquinazolin-3(4H)-yl)acetamide;
2-(1-adamantyl)-N-(4-oxo-2-phenylquinazolin-3(4H)-yl)acetamide;
2-(1-adamantyl)-N-(4-oxoquinazolin-3(4H)-yl)acetamide;
2-(1-adamantyl)-N-(2-methyl-4-oxoquinazolin-3(4H)-yl)acetamide;
2-(1-adamantyl)-N-(2-ethyl-4-oxoquinazolin-3(4H)-yl)acetamide;
(±)-exo-2-bicyclo[2.2.1]hept-2-yl-N-(4-oxoquinazolin-3(4H)-yl)acetamide;
(±)-exo-2-bicyclo[2.2.1]hept-2-yl-N-(2-isopropyl-4-oxoquinazolin-3(4H)-yl)acetamide;
(±)-exo-2-bicyclo[2.2.1]hept-2-yl-N-(4-oxo-2-phenylquinazolin-3(4H)-yl)acetamide;
3-(1-adamantyl)-N-(2-isopropyl-4-oxoquinazolin-3(4H)-yl)propanamide;
2-(1-adamantyl)-N-(2-ethyl-4-oxothieno[2,3-d]pyrimidin-3(4H)-yl)acetamide;
3-(1-adamantyl)-N-(4-oxo-2-phenylquinazolin-3(4H)-yl)propanamide;
2-(1-adamantyl)-N-(6-chloro-4-oxoquinazolin-3(4H)-yl)acetamide;
2-(1-adamantyl)-N-(2-methyl-4-oxothieno[2,3-d]pyrimidin-3(4H)-yl)acetamide;
(±)-endo-2-bicyclo[2.2.1]hept-5-en-2-yl-N-(2-isopropyl-4-oxoquinazolin-3(4H)-yl)acetamide;
(±)-endo-2-bicyclo[2.2.1]hept-5-en-2-yl-N-(4-oxo-2-phenylquinazolin-3(4H)-yl)acetamide;
2-(1-adamantyl)-N-(6-ethyl-4-oxothieno[2,3-d]pyrimidin-3(4H)-yl)acetamide;
2-[3-chloro-1-adamantyl]-N-(2-isopropyl-4-oxoquinazolin-3(4H)-yl)acetamide;
(±)-endo-N-(2-isopropyl-4-oxoquinazolin-3(4H)-yl)bicyclo[2.2.1]heptane-2-carboxamide;
(±)-endo-N-(4-oxo-2-phenylquinazolin-3(4H)-yl)bicyclo[2.2.1]heptane-2-carboxamide;
(±)-exo-2-bicyclo[2.2.1]hept-2-yl-N-(2-ethyl-4-oxothieno[2,3-d]pyrimidin-3(4H)-yl)acetamide;
2-(1-adamantyl)-N-[4-oxo-2-(phenoxymethyl)quinazolin-3(4H)-yl]acetamide;
2-(1-adamantyl)-N-(4-oxothieno[3,2-d]pyrimidin-3(4H)-yl)acetamide;
2-(1-adamantyl)-N-[5-(4-fluorophenyl)-4-oxothieno[2,3-d]pyrimidin-3(4H)-yl]acetamide;
2-(1-adamantyl)-N-(2,4-dioxo-1,4-dihydroquinazolin-3(2H)-yl)acetamide;
(−)-exo-2-[bicyclo[2.2.1]hept-2-yl]-N-(2-isopropyl-4-oxoquinazolin-3(4H)-yl)acetamide;
(+)-exo-2-[bicyclo[2.2.1]hept-2-yl]-N-(2-isopropyl-4-oxoquinazolin-3(4H)-yl)acetamide;
(±)-(endo)-N-(2-isopropyl-4-oxoquinazolin-3(4H)-yl)bicyclo[2.2.1]hept-5-ene-2-carboxamide;
(±)-(exo)-N-(2-isopropyl-4-oxoquinazolin-3(4H)-yl)bicyclo[2.2.1]hept-5-ene-2-carboxamide;
(±)-(endo)-N-(4-oxo-2-phenylquinazolin-3(4H)-yl)bicyclo[2.2.1]hept-5-ene-2-carboxamide;
(±)-(exo)-N-(4-oxo-2-phenylquinazolin-3(4H)-yl)bicyclo[2.2.1]hept-5-ene-2-carboxamide;
2-(1-adamantyl)-N-(7-chloro-2-methyl-4-oxoquinazolin-3(4H)-yl)acetamide;
2-(1-adamantyl)-N-(6-bromo-4-oxoquinazolin-3(4H)-yl)acetamide;
2-(1-adamantyl)-N-(4-oxo-6-phenylthieno[2,3-d]pyrimidin-3(4H)-yl)acetamide;
N-(4-oxo-2-phenylquinazolin-3(4H)-yl)adamantane-2-carboxamide;

(exo,exo)-N-(4-oxo-2-phenylquinazolin-3(4H)-yl)tricyclo[3.2.1.0²,⁴]octane-3-carboxamide;
2-(1-adamantyl)-N-[2-(isopropylthio)-4-oxo-6-phenylthieno[2,3-d]pyrimidin-3(4H)-yl]acetamide;
(±)-2-[(exo)-bicyclo[2.2.1]hept-2-yl]-N-[6-(2-fluorophenyl)-2-isopropyl-4-oxothieno[3,2-d]pyrimidin-3(4H)-yl]acetamide;
(±)-2-[(endo)-bicyclo[2.2.1]hept-2-yl]-N-(2-isopropyl-4-oxoquinazolin-3(4H)-yl)acetamide;
(±)-2-[(endo)-bicyclo[2.2.1]hept-2-yl]-N-(2-ethyl-4-oxoquinazolin-3(4H)-yl)acetamide;
2-(1-adamantyl)-N-(2-methyl-4-oxo-5,6,7,8-tetrahydro[1]benzothieno[2,3-d]pyrimidin-3(4H)-yl)acetamide;
2-(1-adamantyl)-N-(2-methyl-4-oxo-6,7-dihydro-4H-cyclopenta[4,5]thieno[2,3-d]pyrimidin-3(5H)-yl)acetamide;
2-(1-adamantyl)-N-(2,6-dimethyl-4-oxo-5-phenylthieno[2,3-d]pyrimidin-3(4H)-yl)acetamide;
2-(1-adamantyl)-N-(2,6-dimethyl-4-oxothieno[2,3-d]pyrimidin-3(4H)-yl)acetamide;
2-(1-adamantyl)-N-(2-methyl-4-oxo-6,7,8,9-tetrahydro-4H-cyclohepta[4,5]thieno[2,3-d]pyrimidin-3(5H)-yl)acetamide;
2-(1-adamantyl)-N-(2,5,6-trimethyl-4-oxothieno[2,3-d]pyrimidin-3(4H)-yl)acetamide;
2-[3-chloro-1-adamantyl]-N-[2-cyclopropyl-4-oxo-7-(trifluoromethyl)quinazolin-3(4H)-yl]acetamide;
2-[3-chloro-1-adamantyl]-N-(2-cyclopropyl-4-oxoquinazolin-3(4H)-yl)acetamide;
2-[3-chloro-1-adamantyl]-N-(2-ethyl-4-oxothieno[2,3-d]pyrimidin-3(4H)-yl)acetamide;
2-[3-chloro-1-adamantyl]-N-(2-cyclopropyl-7-fluoro-4-oxoquinazolin-3(4H)-yl)acetamide;
N-(2-ethyl-4-oxoquinazolin-3(4H)-yl)-2-oxatricyclo[3.3.1.1³,⁷]decane-1-carboxamide;
endo 2-[bicyclo[3.2.1]oct-3-yl]-N-(2-ethyl-4-oxoquinazolin-3(4H)-yl)acetamide;
2-bicyclo[3.3.1]non-9-yl-N-(2-isopropyl-4-oxoquinazolin-3(4H)-yl)acetamide;
2-bicyclo[3.3.1]non-9-yl-N-(2-ethyl-4-oxoquinazolin-3(4H)-yl)acetamide;
(exo,exo)-N-(2-ethyl-4-oxoquinazolin-3(4H)-yl)tricyclo[3.2.1.0²,⁴]octane-3-carboxamide;
(exo,exo)-N-(2-isopropyl-4-oxoquinazolin-3(4H)-yl)tricyclo[3.2.1.0²,⁴]octane-3-carboxamide;
2-(1-adamantyl)-N-(6-chloro-2-isopropyl-4-oxoquinazolin-3(4H)-yl)acetamide;
2-(1-adamantyl)-N-(6-fluoro-2-isopropyl-4-oxoquinazolin-3(4H)-yl)acetamide;
2-(1-adamantyl)-N-[4-oxo-2-(2,2,2-trifluoroethyl)quinazolin-3(4H)-yl]acetamide;
endo-N-(2-isopropyl-4-oxoquinazolin-3(4H)-yl)-2-7-oxobicyclo[3.3.1]non-3-yl]acetamide;
2-(1-adamantyl)-N-(2-cyclopropyl-4-oxothieno[2,3-c]pyrimidin-3(4H)-yl)acetamide;
2-(1-adamantyl)-N-[2-(diethylamino)-4-oxoquinazolin-3(4H)-yl]acetamide;
2-(1-adamantyl)-N-(2-isopropyl-4-oxothieno[2,3-c]pyrimidin-3(4H)-yl)acetamide; and
(±)-2-[(exo)-bicyclo[2.2.1]hept-2-yl]-N-(2-cyclopropyl-7-fluoro-4-oxoquinazolin-3(4H)-yl)acetamide;
or pharmaceutically acceptable salts, solvates, or salts of solvates thereof.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It will be appreciated that two or more asymmetric centers can be present in the present compounds, hence several diastereomers and enantiomers of the exemplified structures will often be possible, and that pure diastereomers and enantiomers represent preferred embodiments. It is intended that pure diastereomers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein can exhibit the phenomenon of tautomerism. For example, compounds of formula (I), (Ia)-(Id) wherein X is C(O) and $R^2$ is OH can exist as, for example in form (I-i), (I-ii), or equilibrium mixtures thereof:

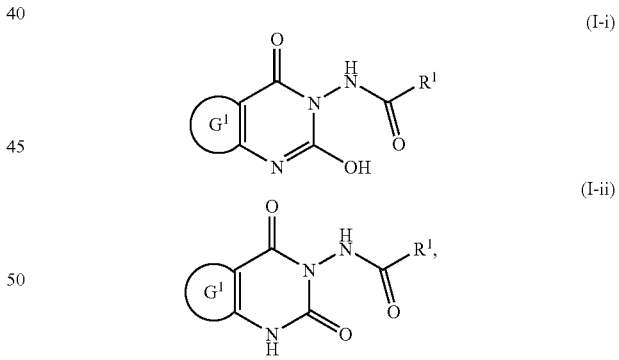

and are thus contemplated within the scope of the invention.

Though structural representations within this specification can show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within drawings or the naming of the compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of KCNQ modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.,* 77, 79-88 (1999)).

In addition, non-radio active isotope containing drugs, such as deuterated drugs called "heavy drugs," can be used for the treatment of diseases and conditions related to the activation of KCNQ channels. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions, potentially altering the pharmcokinetic profile or efficacy relative to the non-isotopic compound.

c. Biological Data (i) In Vitro Assay

The following example describes the assay that can be used to identify compounds that activate KCNQ 2/3 channels.

HEK293 cells stably expressing human KCNQ2 and KCNQ3 were seeded in 96-well, black-walled, clear-bottomed, poly-D-lysine coated plates (BD Biosciences, Bedford, Mass.) at a density of $1 \times 10^5$ cells per well 24 hours before the assay. On the assay day, BTC-AM dye (Invitrogen, Carlsbad, Calif.) was loaded into the cells by replacing the cell culture medium with 100 μL/well of 4 μM dye in DPBS. Dye loading was allowed to proceed for 2 hours at room temperature and then cells were washed twice in 100 μL/well of assay buffer (in mM: 10 HEPES pH 7.3, 5 glucose, 140 Na-gluconate, 2.5 K-gluconate, 3.6 Ca-gluconate, 2 MgSO4, 0.1 Ouabain) to remove unloaded dye. Cells were incubated in 50 μL of assay buffer before loading onto a FLIPR system (Molecular Devices, Sunnyvale, Calif.). Various concentrations of compounds to be assayed were added to the cells in 50 μL of assay buffer and incubated for 4 minutes. The fluorescence signal was initiated by adding 100 μL of assay buffer containing 6 mM $TlNO_3$ and 10 mM $K_2SO_4$. Fluors were excited using the 488-nm line of an argon laser and emission was filtered using a 540±30 nm bandpass filter. Fluorescent signals were recorded for 3 minutes. Responses over baseline values were plotted versus concentrations of test compounds to obtain an $EC_{50}$ value. The maximum response for each test compound was determined relative to the response produced at 10 μM by retigabine. The maximum response of retigabine at 10 μM was set at 100%.

TABLE 1

| Example # | $EC_{50}$ (μM) | Max response |
|---|---|---|
| 1 | 0.138 | 88.85 |
| 2 | 0.198 | 140 |
| 3 | 0.277 | 171 |
| 4 | 2.72 | 60.43 |
| 5 | 0.148 | 122 |
| 6 | 0.341 | 103 |
| 7 | 0.116 | 133 |
| 8 | 0.684 | 108 |
| 9 | 0.115 | 124 |
| 10 | 4.95 | 131 |
| 11 | 0.0906 | 175 |
| 12 | 0.535 | 176 |
| 13 | 0.399 | 172 |
| 14 | 0.691 | 120 |
| 15 | 0.309 | 79.7 |
| 16 | 0.261 | 32.1 |
| 17 | 2.5 | 61.08 |
| 18 | 0.747 | 163 |
| 19 | 2.28 | 130 |

TABLE 1-continued

| Example # | EC$_{50}$ (μM) | Max response |
|---|---|---|
| 20 | 0.438 | 139 |
| 21 | 0.403 | 132 |
| 22 | 0.404 | 124 |
| 23 | 0.54 | 34.33 |
| 24 | 1.13 | 158 |
| 25 | 3.01 | 118 |
| 26 | 2.68 | 140 |
| 27 | 0.846 | 199 |
| 28 | 1.75 | 93.32 |
| 29 | 0.0167 | 136 |
| 30 | 0.0477 | 145 |
| 31 | 0.415 | 140 |
| 32 | 2.23 | 99.17 |
| 33 | 0.84 | 65.4 |
| 34 | 17.32 | 4.46 |
| 35 | >30.0 | 20.78 |
| 36 | >30.0 | 10.8 |
| 37 | >30.0 | 9.51 |
| 38 | >30.0 | −43.5 |
| 39 | >30.0 | −23.48 |
| 40 | >30.0 | 19.2 |
| 41 | >30.0 | 16.97 |
| 42 | 0.0868 | 150 |
| 43 | 0.386 | 150 |
| 44 | 2.01 | 81.85 |
| 45 | >31.6 | 19.6 |
| 46 | 0.454 | 130 |
| 47 | 0.6521 | 56.7 |
| 48 | 10.9 | 89.8 |
| 49 | 0.779 | 65.25 |
| 50 | >31.6 | −0.535 |
| 51 | 0.16 | 152 |
| 52 | 7.91 | 109 |
| 53 | 0.25 | 116 |
| 54 | >31.6 | 5.5 |
| 55 | 0.417 | 150 |
| 56 | 0.104 | 158 |
| 57 | 0.344 | 148 |
| 58 | >31.6 | 11.57 |
| 59 | >31.6 | 16.5 |
| 60 | >31.6 | 58.05 |
| 61 | 0.0307 | 145 |

Majority of the compounds described herein assessed by the above-described assays were found to activate (open) KCNQ 2/3 channels (ii) In Vivo Data Animals Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

Capsaicin-Induced Secondary Mechanical Hypersensitivity:

Rats were allowed to acclimate to the study room for 1 h. They were then briefly restrained, and capsaicin was administered at 10 μg in 10 μl of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds were injected (i.p.) 30 min before testing (150 min post-capsaicin).

Tactile (mechanical) allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53,55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses include an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441. Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats. To evaluate the antinociceptive effects, animals are administered vehicle or test compound and tactile allodynia is assessed 30 minutes after i.p. administration or 1 to 4 hours following p.o. administration.

Tactile allodynia was measured as described above. Compounds tested showed a statistically significant change in paw withdrawal latency versus a saline vehicle at less than about 300 micromoles/kg, such as at less than about 50 micromoles/kg.

Chronic Constriction Injury (CCI) Model of Neuropathic Pain (Bennett Model)

A model of chronic constriction injury-induced (CCI) neuropathic pain was produced by following the method of Bennett and Xie (1988, Pain, 33, 87-107). The right common sciatic nerve was isolated at mid-thigh level, and loosely ligated by 4 chromic gut (5-0) ties separated by an interval of 1 mm. Sham rats underwent the same procedure, but without sciatic nerve constriction. All animals were left to recover for at least 2 weeks and no more than 5 weeks prior to testing of mechanical allodynia. Compounds were injected (i.p.) 30 minutes before testing.

Tactile allodynia was measured as described above. Compounds tested showed a statistically significant change in paw withdrawal latency versus a saline vehicle at less than about 300 micromoles/kg, such as at less than about 50 micromoles/kg.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) can be used to test a compound of the present application The left L5 and L6 spinal nerves of the rat are isolated adjacent to the vertebral column and tightly ligated with a 5-0 silk suture distal to the DRG, and care taken to avoid injury of the L4 spinal nerve. Sham rats undergo the same procedure, but without nerve ligation. All animals are allowed to recover for at least one week and not more than three weeks prior to assessment of tactile allodynia.

d. Methods of using the compounds

One aspect provides methods of using a compound or composition described herein to treat or prevent a disorder, disease or condition of a subject (including human), which disorder, disease, or condition is responsive to modulation of KCNQ potassium channels. In particular, compounds described herein are expected to have utility in the treatment of a disorder, disease or condition which is responsive to modulation of KCNQ potassium channels.

In one group of embodiments, diseases and conditions of humans or other animals that can be treated with activation of KCNQ channels, include, but are not limited to, diseases and conditions involving abnormal neuronal excitability such as but not limited to epilepsy, pain, migraine, anxiety, overactive bladder, schizophrenia, anxiety, and substance abuse.

One embodiment provides methods for treating pain (for example, inflammatory pain, osteoarthritic pain, persistent pain, postoperative pain, cancer pain, neuropathic pain (including diabetic polyneuropathy, HIV-associated sensory neuropathies), migraine, or nociceptive pain) in mammals (including human) in need of such treatment. The methods comprise administering to the mammals therapeutically effective amounts of a compound described herein, or pharmaceutically acceptable salt or solvate thereof. The methods further comprise administration of compounds described herein as a single dose. The methods also comprise repeated or chronic administration of present compounds over a period of days, weeks, months, or longer. In certain embodiments, the method comprises administering to the mammal therapeutically effective amount of a compound described herein, or a pharmaceutically acceptable salt or solvate thereof, in combination with an analgesics (for example, acetaminophen or opioids such as, but not limited to, morphine), or with a nonsteroidal anti-inflammatory drug (NSAID); or administered with a combination of a analgesic and an NSAID. Examples of suitable NSAIDs include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition can optionally include one or more pharmaceutically acceptable carriers.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the active ingredients can be required to achieve the desired therapeutic response. "Repeated or chronic administration" refers to the administration of the compositions described herein daily (i.e., every day) or intermittently (i.e., not every day) over a period of days, weeks, months, or longer. In particular, the treatment of chronic painful conditions is anticipated to require such repeated or chronic administration of the compositions described herein. Compounds of the invention can become more effective upon repeated or chronic administration such that the therapeutically effective doses on repeated or chronic administration can be lower than the therapeutically effective dose from a single administration.

Compounds can also be administered as a pharmaceutical composition comprising the compounds of interest in combination with one or more pharmaceutically acceptable carriers. The phrase "therapeutically effective amount" of the compound of the invention means a sufficient amount of the compound to treat disorders or, or to prevent development of or alleviate to some extent one or more of the symptoms of the condition or disorder being treated, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds can be administered alone, or in combination (i.e. co-administered) with one or more additional pharmaceutical agents. For example, one or more present compounds or pharmaceutically acceptable salts or solvates thereof, can be administered in combination with one or more analgesics (e.g acetaminophen or opioids), or with one or more nonsteroidal anti-inflammatory drug (NSAID), or mixtures thereof. Non limiting examples of suitable NSAIDs include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) can be administered to the patient together, in a single oral dosage composition having a fixed ratio of each active ingredient, such as a tablet or capsule; or each active ingredient can be administered in separate oral dosage formulations.

Separate dosage formulations can be administered at essentially the same time (e.g., concurrently) or at separately staggered times (e.g., sequentially).

Therapeutically effective amounts can be determined by those skilled in the art, and will be adjusted to the requirements of each particular case. Generally, a therapeutically effective amount of a KCNQ modulator will range from a total daily dose, for example in human or other animals, of about 0.01 mg/kg body weight to about 100 mg/kg body weight, preferably of about 0.03 mg/kg body weight to about 30 mg/kg body weight. If desired, the effective daily dose can be divided into multiple doses for purposes of administration. Consequently, single dose compositions can contain such amounts or submultiples thereof to make up the daily dose. It is understood that the effective daily dose can vary with the duration of the treatment.

e. Pharmaceutical Compositions

Pharmaceutical compositions comprising compounds described herein or pharmaceutically acceptable salts or solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts or solvates thereof, and one or more pharmaceutically acceptable carriers, alone or in combination with one or more analgesics (e.g. acetaminophen or opioids), or in combination with one or more nonsteroidal anti-inflammatory drug (NSAID), or a combination of one or more analgesics and one or more NSAID.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like.

Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound can be mixed under sterile conditions with a pharmaceutically acceptable carrier and any needed preservatives, buffers or propellants which can be required. Opthalmic formulations, eye ointments, powders and solutions are also contemplated as being within the scope of this invention.

Compounds described herein can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention can be prepared by a variety of processes well known for the preparation of compounds of this class. For example, the compounds of the invention wherein the groups $G^1$, $R^1$, $R^2$, $R^{2d}$, $R^{2e}$, and X have the meanings as set forth in the summary section unless otherwise noted, can be synthesized as shown in Schemes 1-5.

Abbreviations which have been used in the descriptions of the Schemes and the Examples that follow are: AcOH for acetic acid, DMF for N,N-dimethylformamide, DMSO for dimethyl sulfoxide, Et for ethyl, EtOAc for ethyl acetate, Et₃N for triethylamine, Me for methyl, TFA for trifluoroacetic acid, and THF for tetrahydrofuran.

Compounds of general formula (I) can be prepared using the general method outlined in Scheme 1.

Scheme 1

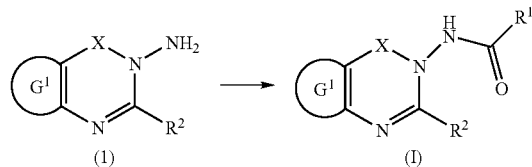

Compounds of formula (1) containing an amine group when treated with compounds of formula $R^1COX^{101}$, wherein $X^{101}$ is chloro, bromo, or OH under coupling conditions known to one skilled in the art, can provide compounds of general formula (I). Typical conditions for the reaction of (1) with compounds of formula $R^1COX^{101}$, wherein $X^{101}$ is chloro or bromo include, but are not limited to, stirring about an equimolar mixture of the compounds in a solvent such as, but not limited to, chloroform, dichloromethane, THF, or mixture thereof, optionally in the presence of a base such as, but not limited to, diisopropylethylamine or pyridine, at about 0° C. to about 30° C. for about 1-30 hours. Acid coupling conditions for compounds of formula $R^1COX^{101}$ wherein $X^{101}$ is —OH and compounds of formula (1), include stirring about an equimolar mixture of the compounds in a solvent such as, but not limited to, THF, N,N-dimethylacetamide, N,N-dimethylformamide, ethyl acetate, pyridine, chloroform, or mixtures thereof, with a coupling reagent, optionally along with a coupling auxiliary, and in the presence or absence of a base. Typical reactions can be carried out at temperatures ranging from about 0° C. to about 80° C. or can be carried out in a microwave reactor to facilitate the coupling. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 1-propanephosphonic acid cyclic anhydride. Non limiting examples of a coupling auxiliary include 1-hydroxy-7-azabenzotriazole (HOAT) and 1-hydroxybenzotriazole hydrate (HOBT). Suitable examples of bases include, but are not limited to, N-methyl morpholine, triethylamine, and diisopropylethylamine.

Certain intermediate compounds of formula (1) wherein X is CO are represented by formula (4). Compounds of general formula (4) can be prepared using the two-step method outlined in Scheme 2.

Scheme 2

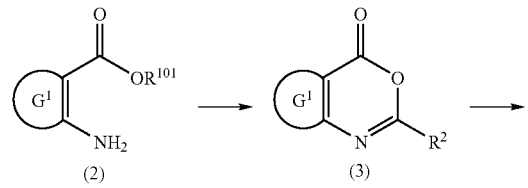

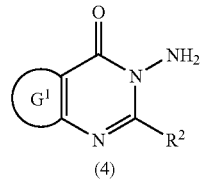

Compounds of formula (2) wherein $R^{101}$ is hydrogen can be converted to compounds of formula (3) by treatment with compounds of formula $R^2COX^{102}$, wherein $X^{102}$ is chloro or bromo, and a base in a suitable solvent at about 0° C. to about 30° C., for about 0.5 to about 24 hours, followed by treatment with acetic anhydride and heating at reflux for 12 to 24 hours in order to effect cyclization. Typical examples of bases include but not limited to, triethylamine, diisopropylethylamine, and pyridine. Examples of suitable solvents include, but are not limited to, chloroform, dichloromethane, THF, and mixtures thereof. Compounds of formula (3) can be converted to compounds of formula (4) by reaction with hydrazine at about room temperature for about 0.5 hour to about 24 hours, followed by heating in a solvent such as, but not limited to, toluene at reflux with removal of water (Dean-Stark apparatus).

Alternatively, compounds of formula (4) can be obtained from compounds of formula (2) wherein $R^{101}$ is an alkyl group by (a) treatment with $R^2COX^{102}$, wherein $X^{102}$ is chloro or bromo and a base (e.g. triethylamine) in a suitable solvent (e.g. THF) at about 0° C. to about 30° C., for about 0.5 to about 24 hours, and (b) reaction of the intermediate from step (a) with hydrazine as described above.

Certain compounds of formula (I) wherein X is CO are represented by formula (7). Compounds of general formula (7) can be prepared using the two-step method outlined in Scheme 3.

Scheme 3

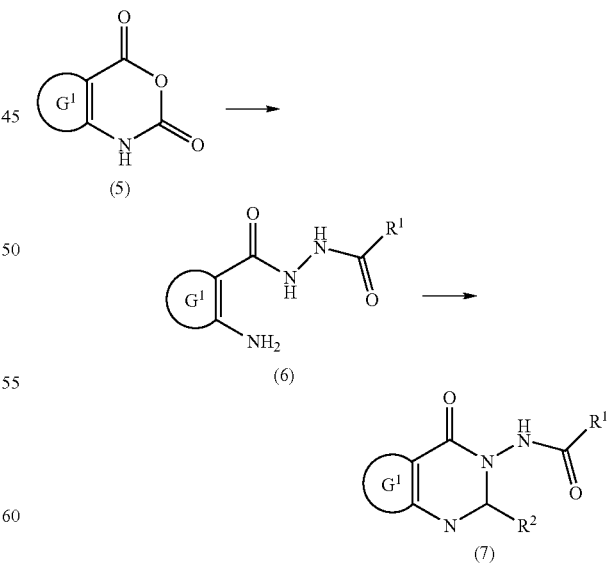

Compounds of formula (5) can be converted to compounds of formula (6) by reaction with an acylhydrazide $R^1CONHNH_2$, in a solvent such as benzene, toluene, xylene, ethanol, or the like, at temperatures from about room temperature to about reflux of the chosen solvent and optionally with either added base (e.g., triethylamine) or acid (e.g., acetic acid). Alternatively, the reaction can be conducted in acetic acid as the reaction solvent at temperatures around 25-50° C. Compounds of formula (6) can be converted to compounds of formula (7) by reaction with an acid $R^2CO_2H$ such as formic acid ($R^2$=H), acetic acid ($R^2$=methyl), and the like, with or without heating; by reaction with an orthoester $R^2C(OEt)_3$ or $R^2C(OMe)_3$ in the presence of an acid such as hydrochloric acid or para-toluenesulfonic acid and heating in a suitable solvent such as dioxane or toluene; by reaction with an acid chloride $R^2COCl$ in the presence of a base such as, but not limited to, pyridine, in a solvent such as, but not limited to, dioxane, and at temperatures from about room temperature to about 100° C.; or by reaction with phosgene or a phosgene equivalent where $R^2$=OH in compounds of formula (7).

Certain compounds of formula (I) wherein X is $SO_2$ are represented by formula (10). Compounds of general formula (10) can be prepared using the general method outlined in Scheme 4.

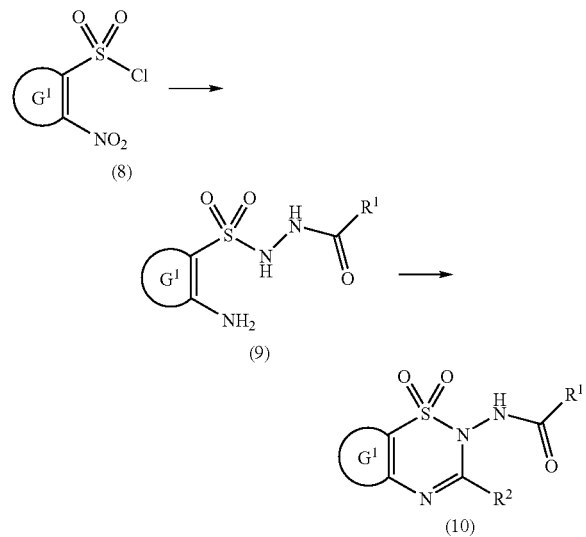

Compounds of formula (8) can be converted to compounds of formula (9) in two steps as follows: (1) reaction with an acylhydrazide $R^1CONHNH_2$, in a solvent such as benzene, toluene, tetrahydrofuran, dimethylformamide or the like, at temperatures from about room temperature to reflux of the chosen solvent and optionally with added base (e.g., triethylamine, pyridine); and (2) reduction of the nitro group to the amino group using reaction conditons known to those skilled in the art, for example, catalytic hydrogenation of the intermediate from step (1) over a palladium-based or platinum-based catalyst in a solvent such as, but not limited to, methanol or ethyl acetate. Compounds of formula (9) can be converted to compounds of formula (10) using conditions from among those illustrated above for the conversion of (6) to (7).

Certain intermediate compounds of formula (1) wherein $R^2$ is $NR^{2d}R^{2e}$ are represented by formula (13). Compounds of general formula (13) can be prepared using the general method outlined in Scheme 5.

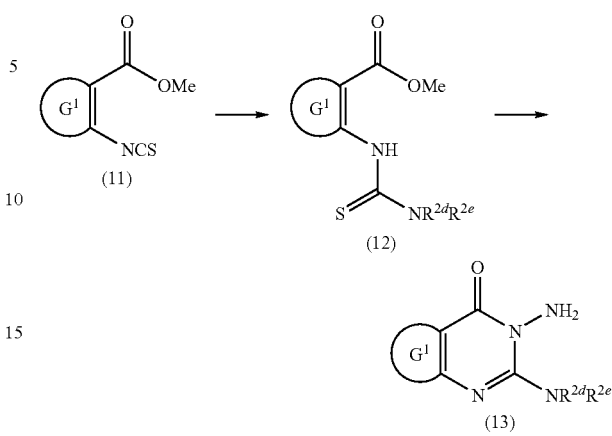

Compounds of formula (11) can be converted to compounds of formula (12) by reaction with a suitable amine of formula $HNR^{2d}R^{2e}$ in a solvent such as dichloromethane, tetrahydrofuran, or chloroform at about room temperature to about 50° C. Compounds of formula (12) can be converted to compounds of formula (13) by reaction first with methyl iodide in a solvent such as, but not limited to, methanol, tetrahydrofuran, or dimethylformamide, at about room temperature to about 100° C., followed by reaction with hydrazine to form the cyclic product (13).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

Following Examples can be used for illustrative purposes and should not be deemed to narrow the scope of the invention.

EXAMPLES

Example 1

2-(2-adamantyl)-N-(2-isopropyl-4-oxoquinazolin-3 (4H)-yl)acetamide

Thionyl chloride (1.72 mL, 23.5 mmol) was added to adamant-2-yl acetic acid (241 mg, 1.24 mmol, prepared as described in J. Med. Chem, (2007), 50(1), 149-164) in a 25 mL round-bottom flask with stir bar. The resulting solution was heated at 80° C. for 1 hour, and then concentrated under vacuum. The residue was taken up in $CH_2Cl_2$ (3 mL) and concentrated under vacuum. This process was repeated twice more to ensure removal of excess thionyl chloride. The residue was taken up in fresh $CH_2Cl_2$ (2 mL) and 3-amino-2-isopropyl-4(3H)-quinazolinone (252 mg, 1.24 mmol) was added. The mixture was stirred at 20-25° C. After 18 hours, diisopropylethylamine (0.40 mL) was added and the solution was stirred for 1 hour longer, and then concentrated under vacuum. The residue was purified by flash chromatography (silica gel, eluted with hexanes-EtOAc, 90:10-70:30). Unreacted quinazolinone (80 mg, 31% recovered) eluted first, followed closely by a second fraction from which crystals precipitated on standing at room temperature for 1 hour. The crystals were collected by filtration and dried at 50° C. under vacuum to provide the title compound (102 mg, 22% yield). $^1H$ NMR (300 MHz, $CDCl_3$) δ ppm 1.32 (2 d, J=6.7 Hz, 6H), 1.58-1.96 (m, 14H), 2.41 (br. t, J=7.3 Hz, 1H), 2.64 (d, J=7.5 Hz, 2H), 3.16 (hept, J=6.7 Hz, 1H), 7.43 (td, J=7.3, 1.2 Hz, 1H), 7.68 (s, 1H), 7.69 (d, J=8.7 Hz, 1H), 7.75 (t, J=7.5 Hz, 1H), 8.21 ppm (d, J=7.5 Hz, 1H); MS (DCI) m/z 380 (M+H)$^+$; Elemental Analysis calculated for $C_{23}H_{29}N_3O_2 \cdot 0.3H_2O$: C, 71.77; H, 7.75; N, 10.92. Found: C, 71.70; H, 7.68; N, 10.76.

Example 2

2-(4-chlorophenyl)-N-(2-hexahydro-2,5-methanopentalen-3a(1H)-yl-4-oxoquinazolin-3(4H)-yl)acetamide Example 2A 2-(hexahydro-2,5-methanopentalen-3a(1H)-yl)-benzo[d][1,3]oxazin-4-one)

Noradamantane-3-carbonyl chloride (0.93 g, 5.04 mmol, Aldrich) was added over 3 minutes to a solution of anthranilic acid (0.68 g, 4.96 mmol) in $CH_2Cl_2$ (5 mL) and triethylamine (0.7 mL, 5.02 mmol). The straw-colored solution was stirred at 20-25° C. for 2.5 hours and then concentrated under vacuum to leave an off-white semisolid. Acetic anhydride (10 mL, 106 mmol) was added, and the mixture was heated at reflux for 14 hours. The reaction mixture was concentrated under vacuum, and the tan solid residue was purified by flash chromatography (silica gel, eluted with hexanes-EtOAc 90:10-70:30) to provide the title compound as a colorless oil that gradually solidified on standing under vacuum (1.04 g, 78%). $^1H$ NMR (300 MHz, $CDCl_3$) δ 1.66-1.74 (m, 4H), 1.95 (dd, J=10.7, 2.8 Hz, 4H), 2.30 (ddd, J=10.5, 1.2, 1.0 Hz, 2H), 2.39 (s, 2H), 2.85 (t, J=6.7 Hz, 1H), 7.48 (td, J=7.5, 1.2 Hz, 1H), 7.59 (d, J=8.7 Hz, 1H), 7.78 (td, J=7.7, 1.6 Hz, 1H), 8.19 ppm (dd, J=7.7, 1.4 Hz, 1H); MS (DCI) m/z 268 (M+H)$^+$.

Example 2B 3-amino-2-(hexahydro-2,5-methanopentalen-3a(1H)-yl)-quinazolin-4(3H)-one)

Anhydrous hydrazine (0.30 mL, 9.56 mmol) was added to a solution of the product of Example 2A (0.79 g, 2.81 mmol) in toluene (10 mL). The solution was stirred at 20-25° C. for 10 hours, then diluted with toluene (15 mL) and heated at reflux under a Dean-Stark trap for 33 hours. The solution was cooled to room temperature and concentrated under vacuum to leave a white solid residue. The residue was purified by flash chromatography (silica gel, eluted with hexanes-EtOAc 70:30-50:50) to provide the title compound as a white solid (0.79 g, 72% yield). $^1H$ NMR (300 MHz, $CDCl_3$) δ ppm 1.64-1.78 (m, 4H), 2.05 (dd, J=10.5, 2.7 Hz, 2H), 2.08-2.18 (m, 2H), 2.40 (br s, 2H), 2.45-2.55 (m, 2H), 2.96 (t, J=6.6 Hz, 1H), 4.73 (s, 2H), 7.44 (ddd, J=8.1, 6.4, 1.7 Hz, 1H), 7.66-7.77 (m, 2H), 8.24 (ddd, J=8.0, 1.4, 0.7 Hz, 1H); MS (DCI) m/z 282 (M+H)$^+$.

Example 2C 2-(4-chlorophenol)-N-(2-hexahydro-2,5-methanopentalen-3a(1H)-yl-4-oxoquinazolin-3(4H)-yl)acetamide The product of Example 2B (272 mg, 0.97 mmol) was added to a solution of 4-chlorophenylacetyl chloride (494 mg, 2.61 mmol, Aldrich) in $CHCl_3$ (8 mL). The clear, colorless solution was stirred at 20-25° C. for 48 hours and then concentrated under vacuum. The residue was purified by flash chromatography (silica gel eluted with hexanes-EtOAc, 80:20-50:50) to provide the title compound as a white solid, which was recrystallized from EtOAc (10 mL) to provide feathery white needles (93 mg, 22% yield). $^1H$ NMR (300 MHz, $CD_3OD$) δ ppm 1.54-1.76 (m, 4H), 1.78-2.04 (m, 4H), 2.16-2.35 (m, 4H), 3.04 (t, J=6.4 Hz, 1H), 3.77 (d, J=14.9 Hz, 1H), 3.85 (d, J=14.9 Hz, 1H), 7.32-7.44 (m, 4H), 7.49 (ddd, J=8.1, 7.0, 1.2 Hz, 1H), 7.68 (dd, J=8.1, 0.7 Hz, 1H), 7.81 (ddd, J=8.2, 7.0, 1.4 Hz, 1H), 8.15 (dd, J=8.1, 1.0 Hz, 1H); MS (DCI) m/z 434/436 (M+H)$^+$; Elemental Analysis Calculated for $C_{25}H_{24}N_3O_2Cl.0.6H_2O$: C, 67.52; H, 5.71; N, 9.45. Found: C, 67.43; H, 5.43; N, 9.43.

Example 3

3-cyclopentyl-N-(2-hexahydro-2,5-methanopentalen-3a(1H)-yl-4-oxoquinazolin-3(4H)-yl)propanamide Thionyl chloride (1.5 mL, 20.55 mmol) was combined with 3-cyclopentylpropionic acid (0.062 mL, 0.44 mmol, Aldrich) and the solution was heated at 65-70° C. for 90 minutes. The solution was cooled to room temperature, and the volatile material removed under vacuum. The residue was diluted with CHCl$_3$ (3 mL) and concentrated again to ensure removal of thionyl chloride. The crude acid chloride was taken up in CHCl$_3$ (3 mL) and stirred at room temperature as the product of Example 2B (100 mg, 0.355 mmol) was added. The mixture was stirred at 20-25° C. for 66 hours and then concentrated under vacuum and the residue was purified by flash chromatography (silica gel, eluted with hexanes-EtOAc, 80:20-50:50) to give a white solid (32 mg), which was recrystallized from aqueous ethanol (1:1) to provide the title compound (22 mg, 15% yield). $^1$H NMR (300 MHz, CDCl$_3$) δ ppm 1.07-1.21 (m, 2H), 1.58-2.06 (m, 17H), 2.23-2.42 (m, 4H), 2.41-2.61 (m, 2H), 2.95 (t, J=6.4 Hz, 1H), 7.40 (s, 1H), 7.43 (ddd, J=8.5, 7.1, 2.0 Hz, 1H), 7.69 (dd, J=8.8, 1.1 Hz, 1H), 7.75 (ddd, J=8.2, 6.9, 1.5 Hz, 1H), 8.21 ppm (dd, J=8.0, 1.5 Hz, 1H); MS (DCI) m/z 406 (M+H)$^+$; Elemental Analysis: calculated for $C_{25}H_{31}N_3O_2.0.3 H_2O$: C, 73.07; H, 7.75; N, 10.23. Found: C, 73.30; H, 7.70; N, 10.01.

Example 4

N-(2-hexahydro-2,5-methanopentalen-3a(1H)-yl-4-oxoquinazolin-3(4H)-yl)acetamide

Acetyl chloride (0.4 mL, 5.30 mmol) was added to a solution of the product of Example 2B (100 mg, 0.36 mmol) in CH$_2$Cl$_2$ (2 mL), and the resulting suspension was stirred at 20-25° C. After 15 hours, methanol (3 mL) was added and the resulting solution was stirred for 3 hours and then concentrated under vacuum. The residue was purified by flash chromatography (silica gel, eluted with hexanes-EtOAc (90:10-50:50) to give a white solid (66 mg) that was further purified by crystallization from ethanol (6 mL) and water (1 mL) to provide the title compound fine white needles (51 mg, 44% yield). $^1$H NMR (300 MHz, CDCl$_3$) δ ppm 1.65-1.76 (m, 4H), 1.88-2.06 (m, 4H), 2.24-2.42 (m, 4H), 2.29 (s, 3H), 2.96 (t, J=6.3 Hz, 1H), 7.40-7.47 (m, 1H), 7.42 (s, 1H), 7.69 (d, J=7.1 Hz, 1H), 7.74 (td, J=6.7, 1.6 Hz, 1H), 8.20 ppm (dd, J=7.7, 1.0 Hz, 1H); MS (DCI) m/z 324 (M+H)$^+$; Elemental Analysis: calculated for $C_{19}H_{21}N_3O_2.H_2O$: C, 66.84; H, 6.79; N, 12.31. Found: C, 67.20; H, 6.80; N, 12.08.

Example 5

2-(1-adamantyl)-N-(2-isopropyl-4-oxoquinazolin-3(4H)-yl)acetamide

3-Amino-2-isopropyl-4(3H)-quinazolinone (Aldrich, 97.5 mg, 0.48 mmol) was dissolved in chloroform (5 mL). 1-Adamantaneacetyl chloride (107.0 mg, 0.50 mmol) and pyridine (100 μL, 1.24 mmol) were added, and the reaction was allowed to stir at ambient temperature for 22 hours. The reaction mixture was concentrated and the residue was purified by preparative HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/min to provide the title compound as a white solid (76.4 mg, 22%). $^1$H NMR (300 MHz, DMSO-d$_6$) δ ppm 1.21-1.26 (m, 6H), 1.60-1.75 (m, 12H), 1.94-1.99 (m, 3H), 2.09-2.20 (m, 2H), 3.09-3.18 (m, 1H), 7.50-7.55 (m, 1H), 7.67 (d, J=7.5 Hz, 1H), 7.82-7.88 (m, 1H), 8.12 (dd, J=7.9, 1.2 Hz, 1H), 10.80 (s, 1H) ppm; MS (DCI/NH$_3$) m/z 380 (M+H)$^+$; Elemental Analysis: Calculated for $C_{23}H_{29}N_3O_2$: C, 72.79; H, 7.70; N, 11.07. Found: C, 72.79; H, 7.81; N, 11.07.

Example 6

2-(1-adamantyl)-N-(4-oxo-2-phenylquinazolin-3(4H)-yl)acetamide

3-Amino-2-phenyl-4(3H)-quinazolinone and 1-adamantaneacetyl chloride were reacted as described in Example 5 to provide the title compound. $^1$H NMR (300 MHz, DMSO-d$_6$) δ ppm 1.11-1.15 (m, 3H), 1.33-1.44 (m, 6H), 1.53-1.57 (m, 3H), 1.72-1.77 (m, 3H), 1.79-1.92 (m, 2H), 7.43-7.50 (m, 3H), 7.58-7.64 (m, 3H), 7.73-7.76 (m, 1H), 7.88-7.64 (m, 1H), 8.18-8.21 (m, 1H), 10.96 (s, 1H) ppm; MS (DCI/NH$_3$) m/z 414 (M+H)$^+$; Elemental Analysis: Calculated for $C_{26}H_{27}N_3O_2.1.15H_2O$: C, 71.92; H, 6.80; N, 9.68. Found: C, 71.93; H, 6.79; N, 9.77.

Example 7

2-(1-adamantyl)-N-(4-oxoquinazolin-3(4H)-yl)acetamide

3-Amino-4(3H)-quinazolinone (158.7 mg, 0.99 mmol) was dissolved in chloroform (5 mL). 1-Adamantaneacetyl chloride (204.1 mg, 0.96 mmol) and pyridine (100 μL, 1.24 mmol) were added, and the reaction was allowed to stir at ambient temperature for 22 hours. The reaction mixture was concentrated and the residue was purified by preparative HPLC on a Waters Nova-Pak® HR C18 6 μm 60 Å Prep-Pak® column (40 mm×100 mm) using a gradient of 10% to 100% acetonitrile in 10 mM aqueous ammonium acetate over 12 minutes at a flow rate of 70 mL/min to provide the title compound as a white solid (264.9 mg, 82%). $^1$H NMR (300 MHz, DMSO-d$_6$) δ ppm 1.60-1.69 (m, 12H), 1.96 (br s, 3H), 7.58-7.63 (m, 1H), 7.74 (d, J=8.3 Hz, 1H), 7.87-7.93 (m, 1H), 8.18-8.20 (m, 2H), 11.12 (s, 1H) ppm; MS (DCI/NH$_3$) m/z 338 (M+H)$^+$; Elemental Analysis: Calculated for $C_{20}H_{23}N_3O_2$: C, 71.19; H, 6.87; N, 12.45. Found: C, 71.11; H, 6.85; N, 12.43.

Example 8

2-(1-adamantyl)-N-(2-methyl-4-oxoquinazolin-3(4H)-yl)acetamide

3-Amino-2-methyl-4(3H)-quinazolinone and 1-adamantaneacetyl chloride were reacted as described in Example 5 to provide the title compound. $^1$H NMR (300 MHz, DMSO-d$_6$) δ ppm 1.60-1.74 (m, 9H), 1.94-1.98 (m, 3H), 2.13 (d, J=1.7 Hz, 1H), 2.39 (s, 3H), 7.50-7.56 (m, 1H), 7.63-7.65 (m, 1H), 7.82-7.88 (m, 1H), 8.11 (dd, J=8.1, 1.0 Hz, 1H), 10.87 (s, 1H) ppm; MS (DCI/NH$_3$) m/z 352 (M+H)$^+$; Elemental Analysis:

Calculated for $C_{20}H_{25}N_3O_2 \cdot H_2O$: C, 68.27; H, 7.37; N, 11.37. Found: C, 68.16; H, 7.40; N, 11.40.

Example 9

2-(1-adamantyl)-N-(2-ethyl-4-oxoquinazolin-3(4H)-yl)acetamide

3-Amino-2-ethyl-4(3H)-quinazolinone and 1-adamantaneacetyl chloride were reacted as described in Example 5 to provide the title compound. $^1$H NMR (300 MHz, DMSO-$d_6$) δ ppm 1.23 (t, J=7.3 Hz, 3H), 1.60-1.74 (m, 12H), 1.92-1.99 (m, 3H), 2.08-2.18 (m, 2H), 2.58-2.79 (m, 2H), 7.50-7.56 (m, 1H), 7.67 (d, J=7.8 Hz, 1H), 7.82-7.88 (m, 1H), 8.12 (dd, J=8.1, 1.4 Hz, 1H), 10.82 (s, 1H) ppm; MS (DCI/NH$_3$) m/z 366 (M+H)$^+$; Elemental Analysis: Calculated for $C_{22}H_{27}N_3O_2 \cdot 0.75H_2O$: C, 69.72; H, 7.58; N, 11.09. Found: C, 69.85; H, 7.77; N, 10.98.

Example 10

(±)-exo-2-bicyclo[2.2.1]hept-2-yl-N-(4-oxoquinazolin-3(4H)-yl)acetamide

Example 10A

2-Norbornaneacetyl chloride

2-Norbornaneacetic acid (Aldrich, Catalog #127264, CAS #1007-01-8, 2.01 g, 13.0 mmol) was dissolved in thionyl chloride (7 mL, 96 mmol). The reaction was heated to reflux for 5 hours. The reaction mixture was concentrated in vacuo to provide the title compound as a colorless oil (2.24 g, 100%) that was used without additional purification.

Example 10B (±)-exo-2-bicyclo[2.2.1]hept-2-yl-N-(4-oxoquinazolin-3(4H)-yl)acetamide 3-Amino-4(3H)-quinazolinone and the product of Example 10A were reacted as described in Example 5 to provide the title compound. $^1$H NMR (300 MHz, DMSO-$d_6$) δ ppm 1.09-1.21 (m, 4H), 1.36-1.56 (m, 4H), 1.85-1.94 (m, 1H), 2.11-2.21 (m, 3H), 2.28-2.36 (m, 1H), 7.58-7.63 (m, 1H), 7.73-7.75 (m, 1H), 7.87-7.92 (m, 1H), 8.17-8.21 (m, 2H), 10.95 (s, 1H) ppm; MS (DCI/NH$_3$) m/z 298 (M+H)$^+$; Elemental Analysis: Calculated for $C_{17}H_{19}N_3O_2 \cdot 0.15H_2O$: C, 68.05; H, 6.48; N, 14.00. Found: C, 68.11; H, 6.49; N, 14.10.

Example 11

(±)-exo-2-bicyclo[2.2.1]hept-2-yl-N-(2-isopropyl-4-oxoquinazolin-3(4H)-yl)acetamide 3-Amino-2-isopropyl-4(3H)-quinazolinone and the product of Example 10A were reacted as described in Example 5 to provide the title compound. $^1$H NMR (300 MHz, DMSO-$d_6$) δ ppm 1.11-1.26 (m, 10H), 1.37-1.55 (m, 4H), 1.88-1.95 (m, 1H), 2.15-2.42 (m, 4H), 3.04-3.15 (m, 1H), 7.53 (t, J=7.5 Hz, 1H), 7.67 (d, J=7.8 Hz, 1H), 7.82-7.88 (m, 1H), 8.11 (dt, J=8.1, 1.9 Hz, 1H), 10.89 (s, 1H) ppm; MS (DCI/NH$_3$) m/z 340 (M+H)$^+$; Elemental Analysis: Calculated for $C_{20}H_{25}N_3O_2 \cdot 0.3H_2O$: C, 69.66; H, 7.48; N, 12.19. Found: C, 69.74; H, 7.53; N, 12.17.

Example 12

(±)-exo-2-bicyclo[2.2.1]hept-2-yl-N-(4-oxo-2-phenylquinazolin-3(4H)-yl)acetamide 3-Amino-2-phenyl-4(3H)-quinazolinone and the product of Example 10A were reacted as described in Example 5 to provide the title compound. $^1$H NMR (300 MHz, DMSO-$d_6$) δ ppm 0.89-1.38 (m, 8H), 1.52-1.61 (m, 1H), 1.86-2.10 (m, 4H), 7.44-7.55 (m, 3H), 7.58-7.64 (m, 3H), 7.74-7.76 (m, 1H), 7.89-7.94 (m, 1H), 8.19 (dt, J=7.8, 1.7 Hz, 1H), 11.04 (s, 1H) ppm; MS (DCI/NH$_3$) m/z 374 (M+H)$^+$; Elemental Analysis: Calculated for $C_{23}H_{23}N_3O_2 \cdot H_2O$: C, 70.57; H, 6.44; N, 10.73. Found: C, 70.44; H, 6.38; N, 10.71.

Example 13

3-(1-adamantyl)-N-(2-isopropyl-4-oxoquinazolin-3(4H)-yl)propanamide

Example 13A 3-(1-Adamantyl)propanoyl chloride 3-(1-Adamantyl)propanic acid was reacted with thionyl chloride as describe in Example 10A to provide the title compound as colorless oil.

Example 13B

3-Amino-2-isopropyl-4(3H)-quinazolinone and the product of Example 13A were reacted as described in Example 5 to provide the title compound. $^1$H NMR (300 MHz, DMSO-$d_6$) δ ppm 1.19-1.25 (m, 6H), 1.40-1.50 (m, 8H), 1.60-1.72 (m, 6H), 1.94-1.98 (m, 3H), 2.31-2.37 (m, 2H), 3.04-3.17 (m, 1H), 7.50-7.55 (m, 1H), 7.67 (d, J=7.8 Hz, 1H), 7.82-7.88 (m, 1H), 8.10 (dd, J=7.9, 1.6 Hz, 1H), 10.92 (s, 1H) ppm; MS (DCI/NH$_3$) m/z 394 (M+H)$^+$; Elemental Analysis: Calculated for $C_{24}H_{31}N_3O_2 \cdot 0.15H_2O$: C, 72.75; H, 7.96; N, 10.16. Found: C, 72.66; H, 7.72; N, 10.58.

Example 14

2-(1-adamantyl)-N-(2-ethyl-4-oxothieno[2,3-d]pyrimidin-3(4H)-yl)acetamide

3-Amino-2-ethylthieno[2,3-d]pyrimidin-4(3H)-one and 1-adamantaneacetyl chloride were reacted as described in Example 5 to provide the title compound. $^1$H NMR (300 MHz, DMSO-$d_6$) δ ppm 1.20 (t, J=7.3 Hz, 3H), 1.59-1.74 (m, 12H), 1.93-1.98 (m, 3H), 2.08-2.18 (m, 2H), 2.56-2.80 (m, 2H), 7.39 (d, J=6.0 Hz, 1H), 7.59 (d, J=6.0 Hz, 1H), 10.83 (s, 1H) ppm; MS (DCI/NH$_3$) m/z 372 (M+H)$^+$; Elemental Analysis: Calculated for $C_{20}H_{25}N_3O_2S$: C, 63.74; H, 6.85; N, 11.15. Found: C, 63.77; H, 6.89; N, 11.13.

Example 15

3-(1-adamantyl)-N-(4-oxo-2-phenylquinazolin-3(4H)-yl)propanamide

3-Amino-2-phenyl-4(3H)-quinazolinone and the product of Example 13A were reacted as described in Example 5 to provide the title compound. $^1$H NMR (300 MHz, DMSO-$d_6$) δ ppm 0.93-1.13 (m, 2H), 1.23-1.33 (m, 6H), 1.51-1.65 (m, 6H), 1.85-1.89 (m, 3H), 1.96-2.08 (m, 2H), 7.44-7.55 (m, 3H), 7.58-7.64 (m, 3H), 7.75 (d, J=7.8 Hz, 1H), 7.89-7.94 (m, 1H), 8.18 (dd, J=8.0, 1.2 Hz, 1H), 11.06 (s, 1H) ppm; MS (DCI/NH$_3$) m/z 428 (M+H)$^+$; Elemental Analysis: Calculated for C$_{27}$H$_{29}$N$_3$O$_2$: C, 75.85; H, 6.84; N, 9.83. Found: C, 75.75; H, 6.97; N, 9.84.

Example 16

2-(1-adamantyl)-N-(6-chloro-4-oxoquinazolin-3 (4H)-yl)acetamide

3-Amino-6-chloro-4(3H)-quinazolinone and 1-adamantaneacetyl chloride were reacted as described in Example 5 to provide the title compound. $^1$H NMR (300 MHz, DMSO-d$_6$) δ ppm 1.60-1.70 (m, 12H), 1.93-1.98 (m, 3H), 2.10 (s, 2H), 7.78 (d, J=8.7 Hz, 1H), 7.93 (dd, J=8.7, 2.4 Hz, 1H), 8.15 (d, J=2.4 Hz, 1H), 8.25 (s, 1H), 11.18 (s, 1H) ppm; MS (DCI/NH$_3$) m/z 372 (M+H)$^+$; Elemental Analysis: Calculated for C$_{20}$H$_{22}$ClN$_3$O$_2$.0.2H$_2$O: C, 63.98; H, 6.01; N, 11.19. Found: C, 3.87; H, 5.85; N, 11.14.

Example 17

2-(1-adamantyl)-N-(2-methyl-4-oxothieno[2,3-d] pyrimidin-3(4H)-yl)acetamide

3-Amino-2-methylthieno[2,3-d]pyrimidin-4(3H)-one and 1-adamantaneacetyl chloride were reacted as described in Example 5 to provide the title compound. $^1$H NMR (300 MHz, DMSO-d$_6$) δ ppm 1.58-1.74 (m, 12H), 1.93-1.98 (m, 3H), 2.08-2.18 (m, 2H), 2.39 (s, 3H), 7.39 (d, J=6.0 Hz, 1H), 7.59 (d, J=6.0 Hz, 1H), 10.89 (s, 1H) ppm; MS (DCI/NH$_3$) m/z 358 (M+H)$^+$; Elemental Analysis: Calculated for C$_{19}$H$_{23}$N$_3$O$_2$S.0.8H$_2$O: C, 61.37; H, 6.67; N, 11.30. Found: C, 61.50; H, 6.86; N, 11.38.

Example 18

(±)-endo-2-bicyclo[2.2.1]hept-5-en-2-yl-N-(2-isopropyl-4-oxoquinazolin-3(4H)-yl)acetamide Example 18A (±)-endo-2-(bicyclo[2.2.1]hept-5-en-2-yl)acetyl chloride Bicyclo[2.2.1]hept-5-en-2-ylacetic acid (Chembridge, catalog #4004417) was reacted with thionyl chloride as described in Example 10A to provide the title compound as colorless semi-solid.

Example 18B (±)-endo-2-bicyclo[2.2.1]hept-5-en-2-yl-N-(2-isopropyl-4-oxoquinazolin-3(4H)-yl)acetamide 3-Amino-2-isopropyl-4(3H)-quinazolinone and the product of Example 18A were reacted as described in Example 5 to provide the title compound. $^1$H NMR (300 MHz, DMSO-d$_6$). δ 0.57-0.67 (m, 1H), 1.19-1.37 (m, 9H), 1.88-1.95 (m, 1H), 2.05-2.24 (m, 2H), 2.80-2.90 (m, 2H), 3.03-3.14 (m, 1H), 6.06 (ddd, J=19.4, 5.6, 2.8 Hz, 1H), 6.22-6.26 (m, 1H), 7.53 (t, J=7.1 Hz, 1H), 7.67 (d, J=7.9 Hz, 1H), 7.82-7.88 (m, 1H), 8.11 (dt, J=7.9, 2.0 Hz, 1H), 10.86 (d, J=11.1 Hz, 1H) ppm; MS (DCI/NH$_3$) m/z 338 (M+H)$^+$; Elemental Analysis: Calculated for C$_{20}$H$_{23}$N$_3$O$_2$.0.4H$_2$O: C, 69.70; H, 6.96; N, 12.19. Found: C, 69.77; H, 6.86; N, 12.12.

Example 19

(±)-endo-2-bicyclo[2.2.1]hept-5-en-2-yl-N-(4-oxo-2-phenylquinazolin-3(4H)-yl)acetamide 3-Amino-2-phenyl-4(3H)-quinazolinone and the product of Example 18A were reacted as described in Example 5 to provide the title compound. $^1$H NMR (300 MHz, DMSO-d) δ ppm. 11-0.45 (m, 1H), 1.06-1.19 (m, 1H), 1.17-1.26 (m, 1H), 1.54-1.69 (m, 1H), 1.79-1.95 (m, 2H), 2.05-2.18 (m, 2H), 2.64-2.76 (m, 1H), 5.78 (ddd, J=77.9, 5.6, 3.0 Hz, 1H), 6.10 (dd, J=5.6, 3.2 Hz, 1H), 7.44-7.53 (m, 3H), 7.59-7.64 (m, 3H), 7.76 (d, J=7.9 Hz, 1H), 7.89-7.95 (m, 1H), 8.18-8.20 (m, 1H), 11.03 (d, J=15.1 Hz, 1H) ppm; MS (DCI/NH$_3$) m/z 372 (M+H)$^+$; Elemental Analysis: Calculated for C$_{23}$H$_{21}$N$_3$O$_2$.0.8H$_2$O: C, 71.60; H, 5.90; N, 10.89. Found: C, 71.92; H, 5.65; N, 10.53.

Example 20

2-(1-adamantyl)-N-(6-ethyl-4-oxothieno[2,3-d]pyrimidin-3(4H)-yl)acetamide

3-Amino-6-ethylthieno[2,3-d]pyrimidin-4(3H)-one and 1-adamantane acetyl chloride were reacted as described in Example 5 to provide the title compound. $^1$H NMR (300 MHz, DMSO-d$_6$) δ ppm. 35 (t, J=7.5 Hz, 1H), 1.64-1.73 (m, 12H), 2.00-2.04 (m, 3H), 2.21 (s, 2H), 2.88 (qd, J=7.5, 1.2 Hz, 1H), 7.17 (t, J=1.2 Hz, 1H), 7.93 (s, 1H), 8.08 (s, 1H) ppm; MS (DCI/NH$_3$) m/z 372 (M+H)$^+$; Elemental Analysis: Calculated for C$_{20}$H$_{25}$N$_3$O$_2$S.0.2H$_2$O: C, 64.04; H, 6.83; N, 11.20. Found: C, 63.91; H, 6.68; N, 11.27.

Example 21

2-[3-chloro-1-adamantyl]-N-(2-isopropyl-4-oxoquinazolin-3(4H)-yl)acetamide

Example 21A (3-Chloroadamantan-1-yl)acetyl chloride (3-Chloroadamantan-1-yl)acetic acid (607.5 mg, 2.66 mmol) was dissolved in thionyl chloride (5 mL, 68.5 mmol). The reaction mixture was heated at reflux for 5 hours. The reaction mixture was cooled and then concentrated in vacuo to provide the title compound as a white solid (646.4 mg, 98%) that was used without additional purification.

Example 21B

2-[3-chloro-1-adamantyl]-N-(2-isopropyl-4-oxoquinazolin-3(4H)-yl)acetamide

3-Amino-2-isopropyl-4(3H)-quinazolinone and the product of Example 21A were reacted as described in Example 5 to provide the title compound. $^1$H NMR (300 MHz, DMSO-d$_6$) δ ppm 1.21-1.26 (m, 6H), 1.51-1.74 (m, 6H), 1.99-2.19 (m, 8H), 2.25 (s, 2H), 3.08-3.17 (m, 1H), 7.51-7.56 (m, 1H), 7.67 (d, J=8.3 Hz, 1H), 7.82-7.88 (m, 1H), 8.13 (dd, J=7.9, 1.6 Hz, 1H), 10.89 (s, 1H) ppm; MS (DCI/NH$_3$) m/z 414

(M+H)⁺; Elemental Analysis: Calculated for $C_{23}H_{28}ClN_3O_2$: C, 66.74; H, 6.82; N, 10.15. Found: C, 66.65; H, 6.82; N, 10.03.

Example 22

(±)-endo-N-(2-isopropyl-4-oxoquinazolin-3(4H)-yl)bicyclo[2.2.1]heptane-2-carboxamide

Example 22A (±)-endo-bicyclo[2.2.1]heptane-2-carbonyl chloride

Bicyclo[2.2.1]heptane-2-carboxylic acid (Alfa Aesar) was reacted with thionyl chloride as described in Example 10A to provide the title compound as colorless semi-solid.

Example 22B (±)-endo-N-(2-isopropyl-4-oxoquinazolin-3(4H)-yl)bicyclo[2.2.1]heptane-2-carboxamide 3-Amino-2-isopropyl-4(3H)-quinazolinone and the product of Example 22A were reacted as described in Example 5 to provide the title compound. ¹H NMR (300 MHz, DMSO-d₆) δ ppm 1.14-1.73 (m, 14H), 2.24-2.25 (m, 1H), 2.64-2.74 (m, 1H), 2.89-2.97 (m, 1H), 3.07-3.14 (m, 1H), 7.53 (t, J=7.5 Hz, 1H), 7.66-7.69 (m, 1H), 7.83-7.88 (m, 1H), 8.01-8.13 (m, 1H), 10.79 (d, J=6.7 Hz, 1H) ppm; MS (DCI/NH₃) m/z 326 (M+H)⁺; Elemental Analysis: Calculated for $C_{19}H_{23}N_3O_2 \cdot 0.25H_2O$: C, 69.17; H, 7.18; N, 12.74. Found: C, 69.13; H, 7.16; N, 12.77.

Example 23

(±)-endo-N-(4-oxo-2-phenylquinazolin-3(4H)-yl)bicyclo[2.2.1]heptane-2-carboxamide 3-Amino-2-phenyl-4(3H)-quinazolinone and the product of Example 22A were reacted as described in Example 5. The residue was purified by preparative HPLC on a Waters Symmetry C8 column (40 mm×100 mm, 7 μm particle size) using a gradient of 10% to 100% acetonitrile:0.1% aqueous TFA over 12 minutes (15 min run time) at a flow rate of 70 mL/min: ¹H NMR (300 MHz, DMSO-d₆) δ ppm 0.15-0.67 (m, 1H), 0.85-1.54 (m, 8H), 2.07-2.14 (m, 2H), 2.57-2.76 (m, 1H), 7.43-7.51 (m, 3H), 7.57-7.67 (m, 3H), 7.75-7.77 (m, 1H), 7.89-7.94 (m, 1H), 8.18-8.21 (m, 1H), 10.90-11.06 (m, 1H) ppm; MS (DCI/NH₃) m/z 360 (M+H)⁺; Elemental Analysis: Calculated for $C_{22}H_{21}N_3O_2 \cdot 0.15$ TFA: C, 71.13; H, 5.66; N, 11.16. Found: C, 71.13; H, 5.61; N, 11.24.

Example 24

(±)-exo-2-bicyclo[2.2.1]hept-2-yl-N-(2-ethyl-4-oxothieno[2,3-d]pyrimidin-3(4H)-yl)acetamide 3-Amino-2-ethylthieno[2,3-d]pyrimidin-4(3H)-one and the product of Example 10A were reacted as described in Example 5 to provide the title compound. ¹H NMR (300 MHz, DMSO-d₆) δ ppm 1.09-1.22 (m, 7H), 1.35-1.50 (m, 4H), 1.84-1.95 (m, 1H), 2.14-2.43 (m, 4H), 2.56-2.81 (m, 2H), 7.38 (d, J=6.0 Hz, 1H), 7.59 (d, J=6.0 Hz, 1H), 10.93 (s, 1H) ppm; MS (DCI/NH₃) m/z 332 (M+H)⁺; Elemental Analysis: Calculated for $C_{17}H_{21}N_3O_2S \cdot 0.85H_2O$: C, 58.89; H, 6.60; N, 12.12. Found: C, 58.91; H, 6.64; N, 12.13.

Example 25

2-(1-adamantyl)-N-[4-oxo-2-(phenoxymethyl)quinazolin-3(4H)-yl]acetamide

3-Amino-2-phenoxymethyl-4(3H)-quinazolinone and 1-adamantaneacetyl chloride were reacted as described in Example 5 to provide the title compound. ¹H NMR (300 MHz, DMSO-d₆) δ ppm 1.50-1.64 (m, 9H), 1.84 (br s, 3H), 2.03-2.15 (m, 2H), 4.96-5.07 (m, 2H), 6.94-7.03 (m, 3H), 7.27-7.34 (m, 2H), 7.59-7.64 (m, 1H), 7.72 (d, J=7.8 Hz, 1H), 7.87-7.92 (m, 1H), 8.18 (dd, J=8.0, 1.2 Hz, 1H), 10.91 (s, 1H) ppm; MS (DCI/NH₃) m/z 444 (M+H)⁺; Elemental Analysis Calculated for $C_{27}H_{29}N_3O_3 \cdot H_2O$: C, 70.26; H, 6.77; N, 9.10. Found: C, 70.17; H, 6.71; N, 9.23.

Example 26

2-(1-adamantyl)-N-(4-oxothieno[3,2-d]pyrimidin-3(4H)-yl)acetamide

3-Amino-3,4-dihydrothieno[3,2-d]pyrimidin-4-one and 1-adamantaneacetyl chloride were reacted as described in Example 1: ¹H NMR (300 MHz, DMSO-d₆) δ ppm 1.57-1.68 (m, 12H), 1.94 (br s, 3H), 2.10 (s, 2H), 7.46 (d, J=5.4 Hz, 1H), 11.15 (s, 1H) ppm; MS (DCI/NH₃) m/z 344 (M+H)⁺.

Example 27

2-(1-adamantyl)-N-[5-(4-fluorophenyl)-4-oxothieno[2,3-d]pyrimidin-3(4H)-yl]acetamide 3-Amino-5-(4-fluorophenyl)thieno[2,3-d]pyrimidin-4(3H)-one (100 mg, 0.383 mmol) was stirred in pyridine (3 mL) at 25° C. 1-Adamantaneacetyl chloride (204.1 mg, 0.96 mmol) was slowly added and the reaction mixture was allowed to stir at 25° C. for 2 hours. The reaction mixture was concentrated to dryness. The resulting material was dissolved in DMSO (3 mL), filtered through a glass microfiber frit and purified by preparative HPLC [Waters XBridge RP18 column, 5 μm, 30×100 mm, flow rate 40 mL/minute, 20-95% gradient of acetonitrile in buffer (0.1 M aqueous ammonium bicarbonate, adjusted to pH 10 with ammonium hydroxide), with UV detection at 254 nm]. Fractions containing the desired product were pooled and concentrated under vacuum to afford the title compound as a white solid (68 mg, 41%). ¹H NMR (400 MHz, DMSO-d₆) δ ppm 1.54-1.70 (m, 12H), 1.92 (br s, 3H), 2.07 (s, 2H), 7.19-7.27 (m, 2H), 7.49-7.56 (m, 2H), 7.62 (s, 1H), 10.90 (br s, 1H); MS (DCI/NH₃) m/z 438 (M+H)⁺. Elemental Analysis calculated for $C_{24}H_{24}FN_3O_2S$: C, 65.88; H, 5.53; N, 9.60. Found C, 65.64; H, 5.48; N, 9.55.

Example 28

2-(1-adamantyl)-N-(2,4-dioxo-1,4-dihydroquinazolin-3(2H)-yl)acetamide

3-Amino-1H-quinazoline-2,4-dione and 1-adamantaneacetyl chloride were reacted as describe in Example 5 to provide the title compound. ¹H NMR (300 MHz, DMSO-d₆) δ ppm 1.58-1.68 (m, 12H), 1.92-1.98 (m, 3H), 1.98-2.07 (m, 2H), 7.21-7.27 (m, 2H), 7.68-7.74 (m, 1H), 7.93-7.96 (m, 1H), 10.34 (s, 1H), 11.51 (s, 1H) ppm; MS (DCI/NH₃) m/z 354 (M+H)⁺; Elemental Analysis: Calculated for 1.58-1.68 (m, 12H), 1.92-1.98 (m, 3H), 1.98-2.07 (m, 2H), 7.21-7.27 (m, 2H), 7.68-7.74 (m, 1H), 7.93-7.96 (m, 1H), 10.34 (s, 1H), 11.51 (s, 1H).

Example 29

(−)-exo-2-[bicyclo[2.2.1]hept-2-yl]-N-(2-isopropyl-4-oxoquinazolin-3(4H)-yl)acetamide The individual enantiomers of Example 11 (700.1 mg) were separated on a Chiralpak AD-H 4.6 mmID×25 cm (hexane/ethyl acetate/diethylamine 85/15/0.1) at 1 mL/min to provide the first-eluting enantiomer (277.5 mg, 40%): $[\alpha]^{20}{}_D=-24°$ (c 0.52, MeOH).

Example 30

(+)-exo-2-[bicyclo[2.2.1]hept-2-yl]-N-(2-isopropyl-4-oxoquinazolin-3(4H)-yl)acetamide The individual enantiomers of Example 11 (700.1 mg) were separated on a Chiralpak AD-H 4.6 mmID×25 cm (hexane/ethyl acetate/diethylamine 85/15/0.1) at 1 mL/min to provide the second-eluting enantiomer (288.1 mg, 41%): $[\alpha]^{20}{}_D=+25°$ (c 0.53, MeOH).

Example 31

(±)-(endo)-N-(2-isopropyl-4-oxoquinazolin-3(4H)-yl)bicyclo[2.2.1]hept-5-ene-2-carboxamide

Example 31A 5-norbornene-2-carbonyl chloride

A solution of 5-norbornene-2-carboxylic acid (Aldrich, mixture of endo and exo, 1.25 g, 9.05 mmol) in dichloromethane (50 mL) was treated with oxalyl chloride (0.99 mL, 11.31 mmol) and a catalytic amount of N,N-dimethylformamide (100 μL). The reaction mixture was stirred at ambient temperature for 2 hours and then solvent and excess oxalyl chloride were removed under reduced pressure to yield the title compound which was used without further purification.

Example 31B (±)-(endo)-N-(2-isopropyl-4-oxoquinazolin-3(4H)-yl)bicyclo[2.2.1]hept-5-ene-2-carboxamide 3-Amino-2-isopropylquinazolin-4(3H)-one (130 mg, 0.639 mmol) and pyridine (0.126 mL, 1.277 mmol) were stirred in CHCl$_3$ (2 mL) at 25° C. Example 31A (100 mg, 0.639 mmol) was slowly added and the reaction mixture was allowed to stir at 25° C. for 2 hours. The reaction mixture was reduced to dryness. The resulting material was dissolved in DMSO (3 mL), filtered through a glass microfiber frit and purified by preparative HPLC [Waters XBridge RP18 column, 5 μm, 30×100 mm, flow rate 40 mL/minute, 20-95% gradient of acetonitrile in buffer (0.1 M aqueous ammonium bicarbonate, adjusted to pH 10 with ammonium hydroxide), with UV detection at 254 nm]. Fractions containing the desired product were pooled, concentrated under vacuum to afford the title compound as a white solid (135 mg, 65%). $^1$H NMR (500 MHz, DMSO-d$_6$) δ ppm 1.18 (dd, J=10.4, 6.7 Hz, 3H), 1.24 and 1.29 (two d, J=6.7 Hz, 3H, amide rotamers), 1.32-1.48 (m, 3H), 1.80-2.03 (m, 1H), 2.90 (br s, 1H), 2.99-3.09 (m, 1H), 3.10-3.19 (m, 1H), 3.36-3.45 (m, 1H), 5.91 and 6.14 (two m, 1H, amide rotamers), 6.05 and 6.23 (two m, 1H, amide rotamers), 7.50-7.55 (m, 1H), 7.64-7.69 (m, 1H), 7.81-7.88 (m, 1H), 8.10 (ddd, J=9.4, 8.0, 1.2 Hz, 1H), 10.79 (br s, 1H); MS (ESI) m/z 324 (M+H)$^+$; Anal. calculated for C$_{19}$H$_{21}$N$_3$O$_2$: C, 70.57; H, 6.55; N, 12.99. Found C, 70.21; H, 6.57; N, 12.99.

Example 32

(±)-(exo)-N-(2-isopropyl-4-oxoquinazolin-3(4H)-yl)bicyclo[2.2.1]hept-5-ene-2-carboxamide Purification of the crude mixture from Example 31B on the HPLC also afforded the title compound as a white solid (30 mg, 15%). $^1$H NMR (500 MHz, DMSO-d$_6$) δ ppm 1.21 (dd, J=6.7, 4.3 Hz, 3 H), 1.24 and 1.28 (two d, J=6.7 Hz, 3 H, amide rotamers), 1.23-1.29 (m, 1 H), 1.30-1.42 (m, 1 H), 1.56 (d, J=7.0 Hz, 1 H), 1.88 and 1.98 (two td, J=7.7, 3.9 Hz, 1 H, amide rotamers), 2.32-2.42 (m, 1 H), 2.93 (br s, 1 H), 3.01 (br s, 1 H), 3.05-3.20 (m, 1H), 3.22 (br s, 1 H), 6.20-6.27 (m, 1 H), 7.51-7.56 (m, 1 H), 7.68 (d, J=7.9 Hz, 1 H), 7.83-7.88 (m, 1 H), 8.11 (ddd, J=9.8, 8.1, 1.4 Hz, 1 H), 10.99 (s, 1 H); MS (ESI) m/z 324 (M+H)$^+$; Anal. calculated for C$_{19}$H$_{21}$N$_3$O$_2$.0.1 H$_2$O: C, 70.18; H, 6.57; N, 12.92. Found C, 70.04; H, 6.46; N, 12.89.

Example 33

(±)-(endo)-N-(4-oxo-2-phenylquinazolin-3(4H)-yl)bicyclo[2.2.1]hept-5-ene-2-carboxamide 3-Amino-2-phenylquinazolin-4(3H)-one (151 mg, 0.639 mmol) and Example 31A (100 mg, 0.639 mmol) were processed as described in Example 31B to afford the title compound as a white solid (117 mg, 51%). $^1$H NMR (500 MHz, DMSO-d$_6$) δ ppm 1.13 and 1.15 (two m, 1 H, amide rotamers), 1.18-1.26 (m, 2 H), 1.65-1.73 (m, 1 H), 2.74 and 2.83 (two m, 1.5 H, amide rotamers), 2.76 and 2.92 (two m, 1.5 H, amide rotamers), 4.47 and 5.85 (two dd, J=5.8, 2.7 Hz, 1 H, amide rotamers), 5.88 and 5.96 (two dd, J=5.6, 2.7 Hz, 1 H, amide rotamers), 7.43-7.67 (m, 6 H), 7.72-7.77 (m, 1 H), 7.87-7.94 (m, 1 H), 8.14-8.21 (m, 1 H); MS (APCI) m/z 358 (M+H)$^+$; Anal. calculated for C$_{22}$H$_{19}$N$_3$O$_2$: C, 73.93; H, 5.36; N, 11.76. Found C, 73.63; H, 5.41; N, 11.69.

Example 34

(±)-(exo)-N-(4-oxo-2-phenylquinazolin-3(4 H)-yl)bicyclo[2.2.1]hept-5-ene-2-carboxamide Purification of the crude material from Example 33 on the HPLC also afforded the title compound as a white solid (29 mg, 13%). $^1$H NMR (500 MHz, DMSO-d$_6$) δ ppm 0.92-1.07 (m, 1 H), 1.12 and 1.35 (two m, 1 H, amide rotamers), 1.13-1.19 (m, 1 H), 1.23 and 1.84 (two td, J=7.7, 3.8 Hz, 1 H, amide rotamers), 2.02-2.13 (m, 1 H), 2.15 and 2.75 (two br s, 1 H, amide rotamers), 2.79 and 3.01 (two br s, 1 H, amide rotamers), 6.00 and 6.13 (two m, 1 H), 6.11-6.14 (m, 1 H), 7.44-7.56 (m, 3 H), 7.57-7.64 (m, 3 H), 7.74-7.79 (m, 1 H), 7.88-7.95 (m, 1 H), 8.17-8.24 (m, 1 H), 11.14 (br s, 1 H); MS (DCI) m/z 358 (M+H)$^+$; Anal. calculated for C$_{22}$H$_{19}$N$_3$O$_2$: C, 73.93; H, 5.36; N, 11.76. Found C, 73.58; H, 5.28; N, 11.58.

Example 35

2-(1-adamantyl)-N-(7-chloro-2-methyl-4-oxoquinazolin-3(4H)-yl)acetamide

3-Amino-7-chloro-2-methylquinazolin-4(3H)-one and 1-adamantaneacetyl chloride were reacted as described in Example 5 to provide the title compound. $^1$H NMR (300 MHz, DMSO-$d_6$) δ ppm 1.59-1.74 (m, 12H), 1.93-1.98 (m, 3H), 2.08-2.18 (m, 2H), 2.40 (s, 3H), 7.57 (dd, J=8.5, 2.0 Hz, 1H), 7.72 (d, J=1.7 Hz, 1H), 8.11 (d, J=8.8 Hz, 1H), 10.90 (s, 1H); MS (DCI/NH$_3$) m/z 386 (M+H)$^+$; Elemental Analysis: Calculated for $C_{21}H_{24}ClN_3O_2 \cdot H_2O$: C, 62.45; H, 6.49; N, 10.40. Found: C, 62.63; H, 6.27; N, 10.36.

Example 36

2-(1-adamantyl)-N-(6-bromo-4-oxoquinazolin-3 (4H)-yl)acetamide

3-Amino-6-bromo-quinazolin-4(3H)-one and 1-adamantaneacetyl chloride were reacted as described in Example 5 to provide the title compound. $^1$H NMR (300 MHz, DMSO-$d_6$) δ ppm 11.60-1.70 (m, 12H), 1.93-1.98 (m, 3H), 2.10 (s, 2H), 7.71 (d, J=8.7 Hz, 1H), 8.05 (dd, J=8.7, 2.4 Hz, 1H), 8.27 (s, 1H), 8.29 (d, J=2.4 Hz, 1H), 11.21 (s, 1H); MS (DCI/NH$_3$) m/z 416 (M+H)$^+$; Elemental Analysis: Calculated for $C_{20}H_{22}BrN_3O_2$: C, 57.70; H, 5.33; N, 10.09. Found: C, 57.63; H, 5.28; N, 10.06.

Example 37

2-(1-adamantyl)-N-(4-oxo-6-phenylthieno[2,3-d] pyrimidin-3(4H)-yl)acetamide

3-Amino-6-phenylthieno[2,3-d]pyrimidin-4(3H)-one and 1-adamantaneacetyl chloride were reacted as described in Example 5 to provide the title compound. $^1$H NMR (300 MHz, DMSO-$d_6$) δ ppm 1.65-1.75 (m, 12H), 2.01-2.05 (m, 3H), 2.23 (s, 2H), 7.35-7.46 (m, 3H), 7.63-7.65 (m, 2H), 7.69 (s, 1H), 7.99 (s, 1H), 8.10 (s, 1H); MS (DCI/NH$_3$) m/z 420 (M+H)$^+$; Elemental Analysis: Calculated for $C_{24}H_{25}N_3O_2S$: C, 68.71; H, 6.01; N, 10.02. Found: C, 68.53; H, 5.65; N, 9.98.

Example 38

N-(4-oxo-2-phenylquinazolin-3(4H)-yl)adamantane-2-carboxamide

A solution of adamantane-2-carboxylic acid (110 mg, 0.61 mmol, prepared as described in J. Med. Chem, (2007), 50(1), 149-164) in thionyl chloride (1.5 mL, 20.6 mmol) was heated at 80° C. for 90 minutes and then cooled to room temperature and concentrated under vacuum. The residue was dissolved in CH$_2$Cl$_2$ (3 mL) and 3-amino-2-phenylquinazolin-4(3H)-one (145 mg, 0.61 mmol, Aldrich) and diisopropylethylamine (0.2 mL, 1.14 mmol) were added. The mixture was stirred at room temperature for 2 hours and concentrated under vacuum. The residue was purified by flash chromatography (SiO$_2$, eluted with hexanes-EtOAc, 90:10-70:30), then by preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/min to provide the title compound as a white powder (56 mg, 23%): $^1$H NMR (300 MHz, CD$_3$OD) δ ppm 1.21 (br. d, J=12.9 Hz, 1 H), 1.31 (br. d, J=12.9 Hz, 1 H), 1.51 (br. d, J=12.7 Hz, 1 H), 1.58-1.72 (m, 3 H), 1.73-1.91 (m, 5 H), 1.90-2.01 (m, 2 H), 2.21 (br. s, 1 H), 2.61 (br. s, 1 H), 7.44-7.56 (m, 3 H), 7.56-7.65 (m, 3 H), 7.76 (d, J=8.3 Hz, 1 H), 7.89 (ddd, J=8.4, 7.0, 1.6 Hz, 1 H), 8.27 (dd, J=7.9, 1.6 Hz, 1 H); MS (DCI) m/z 400 (M+H); Elemental analysis calculated for $C_{25}H_{25}N_3O_2 \cdot 0.7$ H$_2$O: C, 72.86; H, 6.46; N, 10.20. Found: C, 72.72; H, 6.30; N, 10.06.

Example 39

(exo,exo)-N-(4-oxo-2-phenylquinazolin-3(4H)-yl) tricyclo[3.2.1.0$^{2,4}$]octane-3-carboxamide

Example 39A (exo,exo)-tricyclo[3.2.1.0$^{2,4}$]octane-3-carbonyl chloride

A suspension of (exo,exo)-tricyclo[3.2.1.0$^{2,4}$]octane-3-carboxylic acid (305 mg, 2.00 mmol, Matrix) in diethyl ether (2 mL) was stirred at room temperature as thionyl chloride (1.29 mL, 17.6 mmol) was added over 1 minute. The resulting solution was warmed at reflux for 2 hours and then cooled to room temperature and concentrated under vacuum. The residue was diluted with CH$_2$Cl$_2$ (5 mL) and concentrated again to remove excess thionyl chloride. This process was repeated twice. The residue was diluted to 10.00 mL with CH$_2$Cl$_2$ and this solution of the title compound was used in the next step.

Example 39B (exo, exo)-N-(4-oxo-2-phenylquinazolin-3(4H)-yl) tricyclo[3.2.1.0$^{2,4}$]octane-3-carboxamide The solution from Example 39A (5.00 mL) was added to a flask containing 3-amino-2-phenylquinazolin-4-(3H)-one (227 mg, 0.96 mmol, Aldrich), and the resulting slurry was stirred at room temperature for 46 hours. The mixture was concentrated under vacuum and the residue was crystallized from ethanol (6 mL) to provide the title compound in two crops (139 mg, 39%): $^1$ H NMR (300 MHz, CD$_3$OD) δ ppm 0.71 (br. d, J=10.9 Hz, 1 H), 0.92 (br. d, J=10.9 Hz, 1 H), 1.02 (ddd, J=7.3, 1.2, 1.0 Hz, 1 H), 1.19-1.35 (m, 3 H), 1.40-1.52 (m, 2H), 1.54 (t, J=2.4 Hz, 1 H), 2.22 (br. s, 1 H), 2.36 (br. s, 1 H), 7.46-7.63 (m, 6 H), 7.74 (dt, J=8.1, 0.7 Hz, 1 H), 7.88 (ddd, J=8.3, 7.0, 1.7 Hz, 1 H), 8.26 (ddd, J=8.6, 0.9, 0.7 Hz, 1 H); MS (ESI) m/z 372 (M+H)$^+$; Elemental analysis calculated for $C_{23}H_{21}N_3O_2$: C, 74.37; H, 5.70; N, 11.31. Found: C, 74.05; H, 5.55; N, 11.17.

Example 40

2-(1-adamantyl)-N-[2-(isopropylthio)-4-oxo-6-phenylthieno[2,3-d]pyrimidin-3(4H)-yl]acetamide 3-amino-2-(isopropylthio)-6-phenylthieno[2,3-d]pyrimidin-4(3H)-one and 1-adamantaneacetyl chloride were reacted as described in Example 5 to provide the title compound. $^1$H NMR (300 MHz, DMSO-$d_6$) δ ppm 1.38 (t, J=6.7 Hz, 6H), 1.61-1.71 (m, 12H), 1.92-1.97 (m, 3H), 2.05-2.15 (m, 2H), 3.78-3.87 (m, 1H), 7.36-7.49 (m, 3H), 7.75-7.79 (m, 3H), 10.92 (s, 1H); MS (DCI/NH$_3$) m/z 494 (M+H)$^+$; Elemental Analysis: Calculated for $C_{24}H_{25}N_3O_2S$: C, 68.71; H, 6.01; N, 10.02. Found: C, 68.53; H, 5.65; N, 9.98.

Example 41

(±)-2-[(exo)-bicyclo[2.2.1]hept-2-yl]-N-[6-(2-fluorophenyl)-2-isopropyl-4-oxothieno[3,2-d]pyrimidin-3(4H)-yl]acetamide

Example 41A 3-amino-6-(2-fluorophenyl)-2-isopropylthieno[3,2-d]pyrimidin-4(4H)-one Isobutyric anhydride (0.5 mL, 3.0 mmol) was added to a solution of ethyl 3-amino-5-(2-fluorophenyl)thiophene-2-carboxylate (302 mg, 1.14 mmol, prepared as described in WO 2005/066163, p 65-66) in $CH_2Cl_2$ (6 mL) and pyridine (2 mL) and the resulting solution was stirred at room temperature for 26 hours. The reaction mixture was concentrated under vacuum. Additional isobutyric anhydride (1.0 mL) was added and the mixture was heated at 120° C. for 3 hours and then cooled to room temperature and concentrated under vacuum. The residue was taken up in methanol (7 mL) and treated with 10% aqueous KOH (15 mL). The resulting mixture was heated at reflux for 14 hours. The solution was cooled to room temperature and concentrated under vacuum. The residual aqueous solution was stirred at room temperature as 8% aqueous $H_2SO_4$ (15 mL) was added to adjust pH of the solution to about 2. The slurry was stirred at room temperature for 2 hours, with a second addition of 8% $H_2SO_4$ (5 mL) after 30 minutes to maintain the pH of the solution at about 2. The mixture was filtered, and the cake was washed with water (3×4 mL), and dried in air to leave a yellow solid (463 mg). This material was combined with acetic anhydride (4 mL, 42.4 mmol) and the mixture was heated at 100° C. for 5 hours and then cooled to room temperature and concentrated under vacuum to leave a brown solid. This solid was taken up in toluene (30 mL) and hydrazine hydrate (1.5 mL) was added. The mixture was heated at reflux under a Dean Stark trap for 14 hours and then cooled to room temperature and concentrated under vacuum. The residue was purified by chromatography ($SiO_2$ eluted with hexanes-EtOAc 90:10-70:30) to provide the title compound (63 mg, 7%): $^1$H NMR (300 MHz, $CD_3OD$) δ ppm 1.36 (d, J=7.1 Hz, 6 H), 3.91 (hept, J=6.8 Hz, 1 H), 7.25-7.36 (m, 2 H), 7.47 (tdd, J=7.6, 5.4, 1.6 Hz, 1 H), 7.68 (d, J=0.8 Hz, 1 H), 7.83 (td, J=7.9, 1.6 Hz, 1 H); MS (DCI) m/z 304 $(M+H)^+$.

Example 41B (±)-(exo)-2-(bicyclo[2.2.1]heptan-2-yl)acetyl chloride

A solution of (±)-(exo)-2-(bicyclo[2.2.1]heptan-2-yl)acetic acid (1.23 g, 7.98 mmol, Aldrich) in thionyl chloride (5.6 mL, 76 mmol) was heated at reflux for 3 hours. The solution was cooled to room temperature and concentrated under vacuum to provide the title compound as a light amber liquid (1.12 g).

Example 41C (±)-2-[exo)-bicyclo[2.2.1]hept-2-yl]-N-[6-(2-fluorophenyl)-2-isopropyl-4-oxothieno[3,2-d]pyrimidin-3(4H)-yl]acetamide The product of Example 41B (112 mg, 0.65 mmol) was added to a solution of the product of Example 41A (45 mg, 0.15 mmol) in $CH_2Cl_2$ (3 mL). The solution was stirred at room temperature for 42 hours. The mixture was concentrated under vacuum, and the residue was purified by chromatography ($SiO_2$, eluted with hexanes-EtOAc, 90:10-50:50) followed by HPLC on a Waters Nova-Pak® HR C18 6 μm 60 Å Prep-Pak® cartridge column (40 mm×100 mm) using a gradient of 10% to 100% acetonitrile in 10 mM aqueous ammonium acetate over 12 minutes at a flow rate of 70 mL/min to provide the title compound as a white solid (7 mg, 11%): $^1$H NMR (300 MHz, $CDCl_3$) δ ppm 1.12-1.36 (m, 7 H), 1.28-1.37 (m, J=14.3, 6.3 Hz, 6 H), 1.45-1.57 (m, 1 H), 1.98-2.18 (m, 2 H), 2.24-2.38 (m, 2 H), 2.49 (dd, J=14.7, 7.8 Hz, 1 H), 3.15-3.28 (m, 1 H), 7.15-7.25 (m, 2 H), 7.32-7.44 (m, 1 H), 7.66-7.73 (m, 2 H), 7.78 (d, J=4.8 Hz, 1 H); MS (ESI) m/z 440 $(M+H)^+$

Example 42

(±)-2-[(endo)-bicyclo[2.2.1]hept-2-yl]-N-(2-isopropyl-4-oxoquinazolin-3(4H)-yl)acetamide

Example 42A (±)-(endo)-[bicyclo[2.2.1]heptan-2-yl]acetic acid (±)-(endo)-[bicyclo[2.2.1]hept-5-en-2-yl]acetic acid (Chembridge) (6.0 g, 39.4 mmol) was dissolved in ethyl acetate (60 mL). Pd/C (420 mg) was added under $N_2$ atmosphere. The mixture was hydrogenated at 41 psi. for 2 hours. The mixture was filtered, washed with ethyl acetate and concentrated to give the title compound.

Example 42B (±)-(endo)-2-[bicyclo[2.2.1]heptan-2-yl]acetyl chloride

To a mixture of Example 42A (500 mg, 3.24 mmol) and thionyl chloride (1.75 mL, 24.0 mmol) a drop of DMF was added. The reaction was stirred at room temperature for 2 hours. The excess thionyl chloride was evaporated and the residue was dried under vacuum to afford the title compound.

Example 42C (±)-2-[(endo)-bicyclo[2.2.1]hept-2-yl]-N-(2-isopropyl-4-oxoquinazolin-3(4H)-yl)acetamide To a mixture of 3-amino-2-isopropylquinazolin-4(3H)-one (Aldrich) (193 mg, 0.95 mmol) and Example 42B (180 mg, 1.04 mmol) in chloroform (3 mL), pyridine (0.12 ml, 1.42 mmol) was added. The reaction mixture was stirred at room temperature for 12 hours, diluted with $CH_2Cl_2$, washed with aqueous $NaHCO_3$, brine, dried over sodium sulfate, filtered, and concentrated. The residue was purified by Flash Chromatography on $SiO_2$ using an Analogix® Intelliflash280™ (eluted with 0 to 50% EtOAc in Hexanes) to give the title compound. $^1$H NMR (300 MHz, $CDCl_3$) δ ppm 0.70-0.86 (m, 1 H) 1.11-1.22 (m, 1 H) 1.26-1.32 (m, 3 H) 1.32-1.38 (m, 3 H) 1.38-1.50 (m, 5 H) 1.85-2.01 (m, 1 H) 2.16-2.34 (m, 2 H) 2.34-2.45 (m, 1 H) 2.45-2.59 (m, 2 H) 3.09-3.24 (m, 1 H) 7.36-7.48 (m, 1 H) 7.66-7.78 (m, 2 H) 8.21 (d, J=8.1 Hz, 1 H); MS $(ESI^+)$ m/z 340 $(M+H)^+$.

Example 43

(±)-2-[(endo)-bicyclo[2.2.1]hept-2-yl]-N-(2-ethyl-4-oxoquinazolin-3(4 H)-yl)acetamide The product from Example 42B and 3-amino-2-ethylquinazolin-4(3 H)-one (Aldrich) were processed using the method described in Example 42C to afford the title compound. ¹H NMR (300 MHz, CDCl₃) δ ppm 0.66-0.90 (m, 1 H) 1.07-1.23 (m, 1 H) 1.34 (t, J=7.3 Hz, 3H) 1.38-1.61 (m, 5 H) 1.84-2.02 (m, 1 H) 2.15-2.35 (m, 2 H) 2.34-2.45 (m, 1 H) 2.45-2.59 (m, 2 H) 2.69-2.87 (m, 2 H) 7.44 (t, J=7.9 Hz, 1 H) 7.70 (t, J=7.3 Hz, 1 H) 7.74-7.81 (m, 1 H) 8.22 (d, J=9.1 Hz, 1 H); MS (ESI⁺) m/z 326 (M+H)⁺.

Example 44

2-(1-adamantyl)-N-(2-methyl-4-oxo-5,6,7,8-tetrahydro[1]benzothieno[2,3-d]pyrimidin-3(4 H)-yl)acetamide 1-Adamantaneacetyl chloride (BBB-SCl) and 3-amino-2-methyl-5,6,7,8-tetrahydro-3 H-benzo[4,5]thieno[2,3-d]pyrimidin-4-one (Matrix) were processed using the method described in Example 42C to afford the title compound. ¹H NMR (300 MHz, DMSO-d₆) δ ppm 1.57-1.72 (m, 13 H) 1.72-1.85 (m, 4 H) 1.89-1.99 (m, 3 H) 2.08 (m, 1 H) 2.15 (m, 1H) 2.35 (s, 3 H) 2.69-2.78 (m, 2 H) 2.79-2.88 (m, 2 H) 10.78 (s, 1 H); MS (ESI⁺) m/z 412 (M+H)⁺.

Example 45

2-(1-adamantyl)-N-(2-methyl-4-oxo-6,7-dihydro-4H-cyclopenta[4,5]thieno[2,3-d]pyrimidin-3(5H)-yl) acetamide 1-Adamantaneacetyl chloride (BBB-SCl) and 5-amino-6-methyl-1,2,3,5-tetrahydro-8-thia-5,7-diaza-cyclopenta[a]inden-4-one (Matrix) were processed using the method described in Example 42C to afford the title compound. ¹H NMR (300 MHz, DMSO-d₆) δ ppm 1.57-1.77 (m, 14 H) 1.88-2.01 (m, 3 H) 2.03-2.19 (m, 2 H) 2.36 (s, 3 H) 2.38-2.44 (m, 2 H) 2.82-3.00 (m, 4 H) 10.82 (s, 1 H); MS (ESI⁺) m/z 398 (M+H)⁺.

Example 46

2-(1-adamantyl)-N-(2,6-dimethyl-4-oxo-5-phenylthieno[2,3-d]pyrimidin-3(4H)-yl)acetamide 1-Adamantaneacetyl chloride and 3-amino-2,6-dimethyl-5-phenylthieno[2,3-d]pyrimidin-4(3H)-one (Matrix) were processed using the method described in Example 42C to afford the title compound. ¹H NMR (300 MHz, DMSO-d₆) δ ppm 0.87-1.08 (m, 6 H) 1.08 (s, 3 H) 1.19 (d, 3 H) 1.46-1.69 (m, 1 H) 1.75-2.06 (m, 7 H) 2.10-2.25 (m, 1 H) 2.27-2.44 (m, 2 H) 7.43-7.51 (m, 3 H) 7.54 (d, J=7.8 Hz, 1 H) 7.75-7.84 (m, 1 H) 8.08 (dd, J=7.9, 1.19 Hz, 1 H); MS (ESI⁺) m/z 448 (M+H)⁺.

Example 47

2-(1-adamantyl)-N-(2,6-dimethyl-4-oxothieno[2,3-d]pyrimidin-3(4H)-yl)acetamide

1-Adamantaneacetyl chloride and 3-amino-2,6-dimethylthieno[2,3-d]pyrimidin-4(3H)-one (Matrix) were processed using the method described in Example 42C to afford the title compound. ¹H NMR (300 MHz, DMSO-d₆) δ ppm 1.54-1.76 (m, 12 H) 1.89-1.99 (m, 3 H) 2.04-2.18 (m, 2 H) 2.37 (s, 3 H) 2.5 (s, 3 H) 7.09 (s, 1 H) 10.83 (s, 1 H); MS (ESI⁺) m/z 372 (M+H)⁺.

Example 48

2-(1-adamantyl)-N-(2-methyl-4-oxo-6,7,8,9-tetrahydro-4H-cyclohepta[4,5]thieno[2,3-d]pyrimidin-3(5H)-yl)acetamide 1-Adamantaneacetyl chloride and 3-amino-2-methyl-3,5,6,7,8,9-hexahydro-4H-cyclohepta[4,5]thieno[2,3-d]pyrimidin-4-one (Matrix) were processed using the method described in Example 42C to afford the title compound. ¹H NMR (500 MHz, DMSO-d₆) δ ppm 1.49-1.76 (m, 15 H) 1.78-1.89 (m, 2 H) 1.91-2.00 (m, 3 H) 2.08 (d, J=15.0 Hz, 1 H) 2.16 (d, J=15.0 Hz, 1 H) 2.34 (s, 3 H) 2.84 (s, 2 H) 3.11-3.29 (m, 3 H) 10.76 (s, 1 H); MS (ESI⁺) m/z 426 (M+H)⁺.

Example 49

2-(1-adamantyl)-N-(2,5,6-trimethyl-4-oxothieno[2,3-d]pyrimidin-3(4H)-yl)acetamide 1-Adamantaneacetyl chloride and 3-amino-2,5,6-trimethylthieno[2,3-d]pyrimidin-4(3H)-one (Matrix) were processed using the method described in Example 42C to afford the title compound. ¹H NMR (300 MHz, DMSO-d₆) δ ppm 1.55-1.77 (m, 12 H) 1.91-1.98 (m, 3 H) 2.08 (d, J=12.0 Hz, 1 H) 2.15 (d, J=12.0 Hz, 1 H) 2.35 (s, 3 H) 2.36 (s, 6 H) 10.76 (s, 1H); MS (ESI⁺) m/z 386 (M+H)⁺.

Example 50

2-[3-chloro-1-adamantyl]-N-[2-cyclopropyl-4-oxo-7-(trifluoromethyl)quinazolin-3(4H)-yl]acetamide Example 50A 3-Chloro-1-Adamantaneacetyl chloride 3-Chloro-1-adamantaneacetic acid was processed using the method described in Example 42B to afford the title compound.

Example 50B 3-amino-2-cyclopropyl-7-(trifluoromethyl)quinazolin-4(3H)-one

Cyclopropanecarbonyl chloride (2.71 ml, 29.6 mmol) was added to a solution of 2-amino-4-(trifluoromethyl)benzoic acid (2.00 g, 9.75 mmol) in THF (50 mL) followed by pyridine (4.07 ml, 50.3 mmol). The mixture was stirred at 70° C. overnight. The mixture was cooled at 0° C., hydrazine was added, and the reaction was stirred at room temperature for 30 minutes and then at 75° C. for 24 hours. The reaction was cooled at 22° C., diluted with ethyl acetate, washed with aq. NaHCO₃, dried with magnesium sulfate, filtered, and concentrated. The residue was suspended in toluene and concentrated again. The process was repeated to obtain the title compound.

Example 50C

2-[3-chloro-1-adamantyl]-N-[2-cyclopropyl-4-oxo-7-(trifluoromethyl)quinazolin-3(4H)-yl]acetamide The product from Example 50A and Example 50B were processed using the method described in Example 42C to afford the title compound. ¹H NMR (300 MHz, DMSO-d6) δ ppm 0.99-1.12 (m, 3 H) 1.13-1.24 (m, 1 H) 1.49-1.81 (m, 7 H) 1.95-2.13 (m, 6 H) 2.14-2.23 (m, 2 H) 2.24-2.31 (m, 2 H) 7.77 (d, J=9.9 Hz, 1 H) 7.87 (s, 1 H) 8.30 (d, J=8.3 Hz, 1H) 11.15 (s, 1 H); MS (ESI$^+$) m/z 480 (M+H)$^+$.

Example 51

2-[3-chloro-1-adamantyl]-N-(2-cyclopropyl-4-oxo-quinazolin-3(4H)-yl)acetamide

Example 51A 3-amino-2-cyclopropylquinazolin-4(3H)-one

Anthranilic acid (Aldrich) and cyclopropanecarbonyl chloride were processed using the method described in Example 50B to afford the title compound.

Example 51B

2-[3-chloro-1-adamantyl]-N-(2-cyclopropyl-4-oxo-quinazolin-3(4H)-yl)acetamide

The product from Example 50A and Example 51A were processed using the method described in Example 42C to afford the title compound. $^1$H NMR (300 MHz, DMSO-d$_6$) δ ppm 0.96-1.07 (m, 3 H) 1.08-1.17 (m, 1 H) 1.49-1.78 (m, 6 H) 1.96-2.13 (m, 6 H) 2.14-2.23 (m, 3 H) 2.25 (s, 2 H) 7.48 (t, J=6.1 Hz, 1 H) 7.55 (d, J=7.8 Hz, 1 H) 7.75-7.86 (m, 1H) 8.09 (dd, J=8.1, 1.3 Hz, 1 H) 11.01 (s, 1 H); MS (ESI$^+$) m/z 412 (M+H)$^+$.

Example 52

2-[3-chloro-1-adamantyl]-N-(2-ethyl-4-oxothieno[2,3-d]pyrimidin-3(4H)-yl)acetamide The product from Example 50A and 3-amino-2-ethylthieno[2,3-d]pyrimidin-4(3H)-one (Enamine) were processed using the method described in Example 42C to afford the title compound. $^1$H NMR (300 MHz, DMSO-d$_6$) δ ppm 1.20 (t, J=7.3 Hz, 3 H) 1.46-1.81 (m, 6H) 1.94-2.13 (m, 6 H) 2.14-2.23 (m, 2 H) 2.23 (s, 2 H) 2.55-2.86 (m, 2 H) 7.41 (d, J=5.5 Hz, 1 H) 7.59 (d, J=5.5 Hz, 1 H); MS (ESI$^+$) m/z 406 (M+H)$^+$.

Example 53

2-[(3-chloro-1-adamantyl]-N-(2-cyclopropyl-7-fluoro-4-oxoquinazolin-3(4H)-yl)acetamide

Example 53A 3-amino-2-cyclopropyl-7-fluoroquinazolin-4(3H)-one

Cyclopropanecarbonyl chloride and 2-amino-4-fluorobenzoic acid (Aldrich) were processed using the method described in Example 50B to afford the title compound.

Example 53B

2-[(3-chloro-1-adamantyl]-N-(2-cyclopropyl-7-fluoro-4-oxoquinazolin-3(4H)-yl)acetamide The product from Example 50A and Example 53A were processed using the method described in Example 42C to afford the title compound. $^1$H NMR (300 MHz, DMSO-d$_6$) δ ppm 0.96-1.10 (m, 3 H) 1.09-1.24 (m, 1 H) 1.48-1.81 (m, 6 H) 1.94-2.13 (m, 6 H) 2.13-2.22 (m, 3 H) 7.27-7.39 (m, 2 H) 8.08-8.21 (m, 1 H); MS (ESI$^+$) m/z 430 (M+H)$^+$.

Example 54

N-(2-ethyl-4-oxoquinazolin-3(4H)-yl)-2-oxatricyclo[3.3.1.1$^{3,7}$]decane-1-carboxamide

Example 54A

2-Oxa-tricyclo[3.3.1.1$^{3,7}$]decane-1-carboxylic acid methyl ester

The title compound was prepared according to the procedure as described in Richard, Partch; William, Brewster; Bruce, Stokes, *Croatia Chemical Acta* (1969), 58(4), 661-669. MS (ESI$^+$) m/z 197 (M+H)$^+$

Example 54B

2-Oxa-tricyclo[3.3.1.1$^{3,7}$]decane-1-carboxylic acid

To a solution of Example 54A (2.5 g, 12.6 mmol) in methanol/water (1:1, 100 mL), 5 N aqueous NaOH (3.8 mL, 19 mmol) was added. The mixture was stirred at room temperature for 3 hours and then extracted with dichloromethane to remove un-reacted starting material. The aqueous layer was acidified (pH~2) with 6 N aqueous HCl and then extracted with dichloromethane. The combined acidic extracts were dried (Na$_2$SO$_4$), filtered, and concentrated under reduced pressure to afford 1.92 g of the title compound. MS (ESI$^+$) m/z 183 (M+H)$^+$

Example 54C

N-(2-ethyl-4-oxoquinazolin-3(4H)-yl)-2-oxatricyclo[3.3.1.1$^{3,7}$]decane-1-carboxamide To a mixture of 3-amino-2-ethylquinazolin-4(3H)-one (Aldrich, 150 mg, 0.79 mmol) and Example 54B (144 mg, 0.79 mmol) in tetrahydrofuran (10 mL), a solution of 1-propanephosphonic acid cyclic anhydride (Aldrich, 50% w/w in ethyl acetate (0.6 mL, 0.95 mmol) was added followed by triethylamine (0.22 mL, 1.60 mmol). The reaction mixture was stirred at 80° C. overnight and quenched with 1M NaHCO$_3$ (10 mL). The aqueous layer was extracted with EtOAc (2×20 mL). The combined organic layers were dried over Na$_2$SO$_4$, filtered, and concentrated under reduced pressure. The residue was purified by column chromatography using an Analogix® Intelliflash280™ (SiO$_2$, 0-50% of EtOAc in hexanes) to obtain the title compound. $^1$H NMR (300 MHz, DMSO-d$_6$) δ ppm 1.21 (t, J=7.3 Hz, 3 H), 1.64-1.81 (m, 2 H), 1.81-2.07 (m, 8 H), 2.14-2.29 (m, 2 H), 2.51-2.79 (m, 2H), 4.22-4.32 (m, 1 H), 7.49-7.57 (m, 1 H), 7.66 (d, J=7.5 Hz, 1 H), 7.80-7.89 (m, 1 H), 8.09 (dd, J=8.0, 1.2 Hz, 1 H), 10.59 (s, 1 H); MS (ESI$^+$) m/z 354 (M+H)$^+$; Elemental Analysis: Calculated for C$_{20}$ H$_{23}$N$_3$O$_3$: C-67.97; H-6.56, N-11.89. Found: C-67.7; H-6.8; N-11.89.

Example 55 endo 2-[bicyclo[3.2.1]oct-3-yl]-N-(2-ethyl-4-oxo-quinazolin-3(4H)-yl)acetamide

Example 55A

Ethyl 2-(bicyclo[3.2.1]octan-3-ylidene)acetate

To a suspension of NaH (1.55 g, 38.7 mmol, 60% dispersion in oil) in 1,2-dimethoxy ethane (70 mL) at 0° C., triethyl phosphono acetate (8.38 mL, 41.9 mmol) was added. The resulting mixture was stirred 15 minutes at 0° C., 15 minutes at room temperature, and cooled to 0° C. Then, a solution of bicyclo[3.2.1]octan-3-one (Biogene, 4.0 g, 32.2 mmol) in 1,2-dimethoxy ethane (20 mL) was added and the resulting solution was stirred for 5 minutes at 0° C. and then stirred at room temperature overnight. Water was added and the aqueous layer was extracted with ethyl acetate (3×50 mL). The combined organic layers were washed with $H_2O$ (50 mL), brine (50 mL), dried over $MgSO_4$, filtered, and concentrated under reduced pressure. The residue was purified by flash chromatography using an Analogix® Intelliflash280™ (Hex-EtOAc, 0 to 25%) to give the title compound. MS (DCI/$NH_3$) m/z 212 (M+$NH_4$)$^+$

Example 55B endo-ethyl 2-(bicyclo[3.2.1]octan-3-yl)acetate

A mixture of Example 55A (0.85 g, 4.38 mmol) Pd/C (93 mg, 0.09 mmol) in ethanol (20 mL) was stirred under $H_2$ atmosphere using a balloon until the starting material completely consumed. The mixture was filtered and concentrated under reduced pressure to obtain 0.8 g of the title compound. MS (DCI/$NH_3$) m/z 214 (M+$NH_4$)$^+$.

Example 55C endo-2-(bicyclo[3.2.1]octan-3-yl)acetic acid

To a solution of Example 55B (0.8 g, 4.1 mmol) in tetrahydrofuran (8 mL), methanol (4 mL) and water (4 mL), 5M NaOH aqueous solution (4 mL, 20.4 mmol) was added. After stirring at room temperature for 16 hours, the reaction mixture was concentrated to half the volume, washed with methylene chloride (10 mL), neutralized to pH~2 with 3N HCl aqueous solution, and extracted with methylene chloride (3×15 mL). The combined organic layers were dried ($Na_2SO_4$), filtered, and concentrated under reduced pressure to obtain 0.55 g of the title compound. MS (DCI/$NH_3$) m/z 186 (M+$NH_4$)$^+$

Example 55D endo-2-[bicyclo[3.2.1]oct-3-yl]-N-(2-ethyl-4-oxo-quinazolin-3(4H)-yl)acetamide To a mixture of 3-amino-2-ethylquinazolin-4(3H)-one (0.15 g, 0.79 mmol, Aldrich) and Example 55C (0.13 g, 0.79 mmol) in tetrahydrofuran (10 mL), propanephosphonic acid cyclic anhydride (Aldrich, 50% w/w in ethyl acetate (1.4 mL, 2.4 mmol) was added followed by triethylamine (0.552 ml, 4.0 mmol). The reaction mixture was stirred at 80° C. overnight and quenched with 1M $NaHCO_3$ (10 mL). The aqueous layer was extracted with EtOAc (2×20 mL). The combined organic layers were dried over $Na_2SO_4$, filtered, and concentrated under reduced pressure. The residue was purified by column chromatography using an Analogix® Intelliflash280™ ($SiO_2$, 0-50% of EtOAc in hexanes) to obtain 0.07 g of the title compound. $^1$H NMR (300 MHz, DMSO-$d_6$) δ ppm 1.08-1.19 (m, 2 H), 1.22 (t, J=7.5 Hz, 3H), 1.27-1.35 (m, 1 H), 1.36-1.50 (m, 3 H), 1.56-1.73 (m, 4 H), 2.13-2.24 (m, 5 H), 2.54-2.80 (m, 2 H), 7.49-7.56 (m, 1 H), 7.67 (d, J=7.5 Hz, 1 H), 7.84 (d, 1 H), 8.10 (d, 1 H), 10.90 (s, 1 H); MS (ESI$^+$) m/z 340 (M+H)$^+$; Elemental Analysis: Calculated for $C_{20}H_{25}N_3O_2$: C-70.77; H-7.42, N-12.38. Found: C-70.65; H-7.23; N-12.32.

Example 56

2-bicyclo[3.3.1]non-9-yl-N-(2-isopropyl-4-oxo-quinazolin-3(4H)-yl)acetamide

Example 56A

Ethyl 2-(bicyclo[3.3.1]nonan-9-ylidene)acetate

To a suspension of NaH (1.32 g, 52.1 mmol), (60% dispersion in oil) in dimethoxyethane (70 mL) at 0° C., triethyl phosphonoacetate (11.3 mL, 56.4 mmol) was slowly added. The resulting mixture was stirred 15 minutes at 0° C., 15 minutes at room temperature, and cooled to 0° C. A solution of bicyclo[3.3.1]nonan-9-one (Aldrich) (6.0 g, 43.4 mmol) in dimethoxyethane (20 mL) was then added and the resulting solution was stirred for 5 minutes at 0° C. and warmed to room temperature overnight. Water was added and the aqueous layer was extracted with ethyl acetate (3×). The combined organic layers were washed with water, brined, dried over $MgSO_4$, filtered, and the solvent was evaporated. The crude product was purified by flash chromatography using an Analogix® Intelliflash280™ (Hexanes-EtOAc, 0 to 25%) to give the title compound.

Example 56B

Ethyl 2-(bicyclo[3.3.1]nonan-9-yl)acetate

Example 60A (8.75 g, 42.0 mmol) was dissolved in ethyl acetate (30 mL). Pd/C (894 mg) was added under $N_2$ atmosphere. The mixture was hydrogenated at 41 psi for 2 hours. The mixture was filtered, washed with ethyl acetate and concentrated to give the title compound.

Example 56C 2-(Bicyclo[3.3.1]nonan-9-yl)acetic acid

To a solution of Example 56B (8.5 g 40.4 mmol) in methanol (100 mL), aqueous NaOH (50%, 25 mL) was added. The reaction was stirred at room temperature for 24 hours. Methanol was evaporated and the mixture was extracted with ether and then acidified with 6N HCl to pH 2. The mixture was extracted with ether (2×50 mL), the organic layer was dried with magnesium sulfate, filtered, and concentrated to afford the title compound.

Example 56D 2-(Bicyclo[3.3.1]nonan-9-yl)acetyl chloride

Example 56C was processed using the method described in Example 42B to afford the title compound.

Example 56E 2-bicyclo[3.3.1]non-9-yl-N-(2-isopropyl-4-oxo-quinazolin-3(4H)-yl)acetamide The product from Example 56D and 3-amino-2-isopropylquinazolin-4(3H)-one (Aldrich) were processed using the method described in Example 42C to afford the title compound. $^1$H NMR (300 MHz, DMSO-$d_6$) δ ppm 1.20 (d, J=6.7 Hz, 3 H) 1.24 (d, J=6.7 Hz, 3 H) 1.43-1.59 (m, 4 H) 1.65-1.95 (m, 10 H) 1.97-2.08 (m, 1 H) 2.51-2.56 (m, 2 H) 3.02-3.14 (m, 1 H) 7.53 (t, J=6.9 Hz, 1 H) 7.67 (d, J=8.3 Hz, 1 H) 7.79-7.89 (m, 1 H) 8.11 (dd, J=7.9, 1.5 Hz, 1 H) 10.94 (s, 1 H); MS (ESI$^+$) m/z 368 (M+H)$^+$.

Example 57

2-bicyclo[3.3.1]non-9-yl-N-(2-ethyl-4-oxoquinazolin-3(4H)-yl)acetamide

The product from Example 56D and 3-amino-2-ethylquinazolin-4(3H)-one (Aldrich) were processed using the method described in Example 42C to afford the title compound. $^1$H NMR (300 MHz, DMSO-d$_6$) δ ppm 1.22 (t, J=7.5 Hz, 1 H) 1.40-1.59 (m, 4 H) 1.63-1.97 (m, 10 H) 1.99-2.09 (m, 1 H) 2.51-2.56 (m, 2 H) 2.56-2.67 (m, 1 H) 2.67-2.80 (m, 1 H) 7.53 (t, J=7.0 Hz, 1 H) 7.67 (d, J=7.8 Hz, 1 H) 7.80-7.89 (m, 1 H) 8.11 (dd, J=8.1, 1.4 Hz, 1 H) 10.95 (s, 1 H); MS (ESI$^+$) m/z 354 (M+H)$^+$.

Example 58

(exo,exo)-N-(2-ethyl-4-oxoquinazolin-3(4H)-yl) tricyclo[3.2.1.0$^{2,4}$]octane-3-carboxamide

Example 58A (exo,exo)-Tricyclo[3.2.1.0$^{2,4}$]octane-3-carboxylic acid chloride (exo,exo)-Tricyclo[3.2.1.0$^{2,4}$]octane-3-carboxylic acid (Matrix) was processed using the method described in Example 42B to afford the title compound.

Example 58B (exo,exo)-N-(2-ethyl-4-oxoquinazolin-3(4H)-yl) tricyclo[3.2.1.0$^{2,4}$]octane-3-carboxamide The product from Example 58A and 3-amino-2-ethylquinazolin-4(3H)-one (Aldrich) were processed using the method described in Example 42C to afford the title compound. $^1$H NMR (300 MHz, DMSO-d$_6$) δ ppm 0.74 (d, J=10.8 Hz, 1 H) 0.96 (d, J=10.5 Hz, 1 H) 1.21 (t, J=7.4 Hz, 3 H) 1.25-1.33 (m, 4 H) 1.40-1.52 (m, 2 H) 1.77-1.87 (m, 1 H) 2.34-2.44 (m, 2 H) 2.53-2.64 (m, 1 H) 2.64-2.81 (m, 1 H) 7.52 (t, J=7.9 Hz, 1 H) 7.66 (d, J=7.8 Hz, 1 H) 7.84 (t, J=7.8 Hz, 1 H) 8.09 (dd, J=7.9, 1.2 Hz, 1 H) 10.96 (s, 1 H); MS (ESI$^+$) m/z 324 (M+H)$^+$.

Example 59

(exo,exo)-N-(2-isopropyl-4-oxoquinazolin-3(4H)-yl) tricyclo[3.2.1.0$^{2,4}$]octane-3-carboxamide The product from Example 58A and 3-amino-2-isopropylquinazolin-4(3H)-one (Aldrich) were processed using the method described in Example 42C to afford the title compound. $^1$H NMR (300 MHz, DMSO-d$_6$) δ ppm 0.74 (d, J=10.5 Hz, 1 H) 0.97 (d, J=10.9 Hz, 1 H) 1.18 (d, J=6.8 Hz, 3 H) 1.24 (d, J=6.8 Hz, 3 H) 1.26-1.33 (m, 4 H) 1.42-1.52 (m, 2 H) 1.77-1.85 (m, 1 H) 2.40 (s, 2 H) 3.01-3.14 (m, 1 H) 7.46-7.56 (m, 1 H) 7.66 (d, J=7.5 Hz, 1 H) 7.78-7.88 (m, 1 H) 8.09 (dd, J=8.1, 1.0 Hz, 1 H) 10.95 (s, 1 H); MS (ESI$^+$) m/z 338 (M+H)$^+$.

Example 60 endo-N-(2-isopropyl-4-oxoquinazolin-3(4H)-yl)-2-7-oxobicyclo[3.3.1]non-3-yl]acetamide

Example 60A ethyl 2-(7-oxobicyclo[3.3.1]nonan-3-ylidene)acetate

Commercially available, bicyclo[3.3.1]nonane-3,7-dione (Aldrich), NaH and triethyl phosphonoacetate were reacted as described in Example 55A to provide the title compound. MS (DCI/NH$_3$) m/z 240 (M+NH$_4$)$^+$

Example 60B endo-ethyl 2-(7-oxobicyclo[3.3.1]nonan-3-yl)acetate

Example 60A, pd/C and H$_2$ gas were reacted as described in Example 55B to provide the title compound. MS (DCI/NH$_3$) m/z 242 (M+NH$_4$)$^+$

Example 60C endo-2-(7-oxobicyclo[3.3.1]nonan-3-yl)acetic acid

Example 60B and NaOH were reacted as described in Example 55C to provide the title compound. MS (DCI/NH$_3$) m/z 214 (M+NH$_4$)$^+$

Example 60D endo-N-(2-isopropyl-4-oxoquinazolin-3(4H)-yl)-2-[7-oxobicyclo[3.3.1]non-3-yl]acetamide Commercially available 3-Amino-2-isopropyl-4(3H)-quinazolinone, Example 60C, and 1-propanephosphonic acid cyclic anhydride were reacted as described in Example 55D to provide the title compound. $^1$H NMR (400 MHz, DMSO-d$_6$) δ ppm 0.74-0.91 (m, 2 H), 1.20 (d, J=6.7 Hz, 3 H), 1.23 (d, J=7.0 Hz, 3 H), 1.64 (m, 1 H), 1.84 (m, 1 H), 2.12 (m, 7 H), 2.50 (m, 4 H), 3.00-3.14 (m, 1 H), 7.50-7.56 (m, 1 H), 7.67 (d, J=7.9 Hz, 1 H), 7.85 (dd, 1H), 8.10 (dd, J=7.9, 1.2 Hz, 1 H), 10.91 (s, 1 H); MS (ESI$^+$) m/z 382 (M+H)$^+$.

Example 61

(±)-2-[(exo)-bicyclo[2.2.1]hept-2-yl]-N-(2-cyclopropyl-7-fluoro-4-oxoquinazolin-3(4H)-yl)acetamide

Example 61A (±)-(exo)-2-(bicyclo[2.2.1]heptan-2-yl)acetyl chloride (±)-(exo)-2-norbonaneacetic acid (Aldrich) was processed using the method described in Example 42B to afford the title compound.

Example 61B (±)-2-[(exo)-bicyclo[2.2.1]hept-2-yl]-N-(2-cyclopropyl-7-fluoro-4-oxoquinazolin-3(4H)-yl)acetamide Example 53A and Example 61A were processed using the method described in Example 42C to afford the title compound. $^1$H NMR (300 MHz, DMSO-$d_6$) δ ppm 0.95-1.25 (m, 8 H) 1.31-1.54 (m, 4 H) 1.81-1.97 (m, 1 H) 2.10-2.26 (m, 4 H) 2.25-2.45 (m, 1H) 7.33 (d, J=9.2 Hz, 1 H) 7.35-7.40 (m, 1 H) 8.01-8.22 (m, 1 H) 11.02 (s, 1 H); MS (ESI$^+$) m/z 356 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:

1. A compound having formula (I-a):

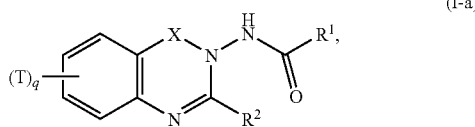

(I-a)

or a stereoisomer thereof, or a pharmaceutically acceptable salt of the compound or stereoisomer, wherein each T is independently $G^a$, alkyl, halogen, haloalkyl, oxo, —CN, —NO$_2$, —OR$^a$, —NR$^a$R$^b$, —SR$^a$, —S(O)R$^a$, —S(O)$_2$R$^a$, —C(O)R$^a$, —C(O)OR$^a$, —C(O)NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, or —(CR$^{za}$R$^{zb}$)$_m$-$G^a$;

q is 0, 1, 2, 3, or 4;

X is C(O);

R$^1$ is $G^{1a}$ or —(CR$^{1a}$R$^{1b}$)$_n$-$G^{1a}$;

R$^2$ is alkyl;

$G^{1a}$ is polycyclic cycloalkyl which is unsubstituted or substituted with 1, 2, 3, or 4 substituents independently selected from the group consisting of $G^a$, alkyl, halogen, haloalkyl, oxo, —CN, —NO$_2$, —OR$^a$, —NR$^a$R$^b$, —SR$^a$, —S(O)R$^a$, —S(O)$_2$R$^a$, —C(O)R$^a$, —C(O)OR$^a$, —C(O)NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$, —(CR$^{za}$R$^{zb}$)$_m$—SR$^a$, —(CR$^{za}$R$^{zb}$)$_m$—S(O)$_2$R$^a$, —(CR$^{za}$R$^{zb}$)$_m$—C(O)R$^a$, and —(CR$^{za}$R$^{zb}$)$_m$—C(O)NR$^a$R$^b$;

$G^a$, at each occurrence, is independently aryl or $C_3$—$C_6$ cycloalkyl; each of which is independently unsubstituted or substituted with 1, 2, or 3 substituents selected from the group consisting of alkyl, halogen, haloalkyl, oxo, —CN, —NO$_2$, —OR$^a$, —NR$^a$R$^b$, —SR$^a$, —S(O)R$^a$, —S(O)$_2$R$^a$, —C(O)R$^a$, —C(O)OR$^a$, —C(O)NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—C(O)R$^a$, —(CR$^{za}$R$^{zb}$)$_m$—C(O)OR$^a$, and —(CR$^{za}$R$^{zb}$)$_m$—C(O)NR$^a$R$^b$;

R$^a$ and R$^b$, at each occurrence, are each independently hydrogen, alkyl, or haloalkyl;

R$^{1a}$ and R$^{1b}$, at each occurrence, are each independently hydrogen, alkyl, halogen, or haloalkyl;

R$^{za}$ and R$^{zb}$, at each occurrence, are each independently hydrogen, alkyl, halogen, or haloalkyl; and m and n, at each occurrence, are each independently 1, 2, 3, or 4.

2. The compound or stereoisomer according to claim 1, or a pharmaceutically acceptable salt of the compound or stereoisomer, wherein $G^{1a}$ is optionally substituted hexahydro-2,5-methano-3a(1 H)-pentalene, optionally substituted adamantane, unsubstituted bicyclo[2.2.1]heptane, unsubstituted bicyclo[2.2.1]heptene, optionally substituted oxatricyclo[3.3.1.1$^{3,7}$]decane, unsubstituted bicyclo[3.2.1]octane, bicyclo[3.3.1]nonane unsubstituted or substituted with one oxo group, or unsubstituted tricyclo[3.2.1.0$^{2,4}$]octane.

3. The compound or stereoisomer according to claim 1, or a pharmaceutically acceptable salt of the compound or stereoisomer, wherein the compound or stereoisomer is selected from the group consisting of:
2-(2-adamantyl)-N-(2-isopropyl-4-oxoquinazolin-3(4H)-yl)acetamide;
2-(1-adamantyl)-N-(2-isopropyl-4-oxoquinazolin-3(4H)-yl)acetamide;
2-(1-adamantyl)-N-(2-methyl-4-oxoquinazolin-3(4H)-yl)acetamide;
2-(1-adamantyl)-N-(2-ethyl-4-oxoquinazolin-3(4H)-yl)acetamide;
(±)-exo-2-bicyclo[2.2.1]hept-2-yl-N-(2-isopropyl-4-oxoquinazolin-3(4H)-yl)acetamide;
3-(1-adamantyl)-N-(2-isopropyl-4-oxoquinazolin-3(4H)-yl)propanamide;
(±)-endo-2-bicyclo[2.2.1]hept-5-en-2-yl-N-(2-isopropyl-4-oxoquinazolin-3(4H)-yl)acetamide;
2-[3-chloro-1-adamantyl]-N-(2-isopropyl-4-oxoquinazolin-3(4H)-yl)acetamide;
(±)-endo-N-(2-isopropyl-4-oxoquinazolin-3(4H)-yl)bicyclo[2.2.1]heptane-2-carboxamide;
(−)-exo-2-[bicyclo[2.2.1]hept-2-yl]-N-(2-isopropyl-4-oxoquinazolin-3(4H)-yl)acetamide;
(+)-exo2-[bicyclo[2.2.1]hept-2-yl]-N-(2-isopropyl-4-oxoquinazolin-3(4H)-yl)acetamide;
(±)-(endo)-N-(2-isopropyl-4-oxoquinazolin-3(4H)-yl)bicyclo[2.2.1]hept-5-ene-2-carboxamide;
(±)-(exo)-N-(2-isopropyl-4-oxoquinazolin-3(4H)-yl)bicyclo[2.2.1]hept-5-ene-2-carboxamide;
2-(1-adamantyl)-N-(7-chloro-2-methyl-4-oxoquinazolin-3(4H)-yl)acetamide;
(±)-2-[(endo)-bicyclo[2.2.1]hept-2-yl]-N-(2-isopropyl-4-oxoquinazolin-3(4H)-yl)acetamide;
(±)-2-[(endo)-bicyclo[2.2.1]hept-2-yl]-N-(2-ethyl-4-oxoquinazolin-3(4H)-yl)acetamide;
N-(2-ethyl-4-oxoquinazolin-3(4H)-yl)-2-oxatricyclo[3.3.1.1$^{3,7}$]decane-1-carboxamide;
endo 2-[bicyclo[3.2.1]oct-3-yl]-N-(2-ethyl-4-oxoquinazolin-3(4H)-ypacetamide;
2-bicyclo[3.3.1]non-9-yl-N-(2-isopropyl-4-oxoquinazolin-3(4H)-yl)acetamide;
2-bicyclo[3.3.1]non-9-yl-N-(2-ethyl-4-oxoquinazolin-3(4H)-yl)acetamide;
(exo,exo)-N-(2-ethyl-4-oxoquinazolin-3(4H)-yl)tricyclo[3 .2.1.0$^{2,4}$]octane-3-carboxamide;
(exo,exo)-N-(2-isopropyl-4-oxoquinazolin-3(4H)-yl)tricyclo[3.2.1.0$^{2,4}$]octane-3-carboxamide; and
endo-N-(2-isopropyl-4-oxoquinazolin-3(4H)-yl)-2-7-oxobicyclo[3.3.1]non-3-yl)acetamide.

4. A pharmaceutical composition comprising a therapeutically effective amount of a compound or stereoisomer of formula (I-a) according to claim 1, or a pharmaceutically acceptable salt of the compound or stereoisomer, in combination with a pharmaceutically acceptable carrier.

5. A method for treating pain in a subject in need of such treatment comprising administering to the subject a therapeutically effective amount of a compound or stereoisomer of formula (I-a) according to claim 1, or a pharmaceutically acceptable salt of the compound or stereoisomer, alone or in combination with a pharmaceutically acceptable carrier.

6. A method for treating epilepsy, migraine, overactive bladder, schizophrenia, or anxiety in a subject in need thereof, said method comprises administering to the subject a therapeutically effective amount of a compound or stereoisomer of formula (I-a) according to claim 1, or a pharmaceutically acceptable salt of the compound or stereoisomer, alone or in combination with a pharmaceutically acceptable carrier.

7. A method of activating KCNQ channels, comprising administering to a subject in need thereof a therapeutically effective amount of a compound or stereoisomer of formula (I-a) according to claim 1, or a pharmaceutically acceptable salt of the compound or stereoisomer, alone or in combination with a pharmaceutically acceptable carrier.

\* \* \* \* \*